United States Patent [19]

Masai et al.

[11] Patent Number: 5,021,435
[45] Date of Patent: Jun. 4, 1991

[54] CERTAIN PYRIDYL-THIAZOLIDIN-4-ONE HAVING ANTI-ULCER ACTIVITY

[75] Inventors: Naruhito Masai, Sakai; Masao Enomoto, Osaka; Atsuyuki Kojima, Takarazuka; Hiroaki Masumori; Nobuyuki Hara, both of Ibaraki; Youichi Hara, Suita; Shigeaki Morooka, Kawanishi, all of Japan

[73] Assignee: Sumitomo Pharmaceuticals Company, Limited, Osaka, Japan

[21] Appl. No.: 297,313

[22] Filed: Jan. 17, 1989

[30] Foreign Application Priority Data

Jan. 22, 1988 [JP] Japan .................................. 63-12380

[51] Int. Cl.$^5$ .................. C07D 417/04; A61K 31/44
[52] U.S. Cl. .................................... 514/342; 546/280
[58] Field of Search ...................... 546/280; 514/342

[56] References Cited

U.S. PATENT DOCUMENTS

| | | | |
|---|---|---|---|
| 2,910,479 | 10/1959 | deStevens | 546/280 |
| 3,705,153 | 12/1972 | Kaneko et al. | 548/204 |
| 4,017,628 | 4/1977 | Nitidandhaprabhas | 514/342 |
| 4,406,905 | 9/1983 | Zahner et al. | 514/342 |
| 4,434,172 | 2/1984 | Kawasaki et al. | 514/369 |
| 4,501,746 | 2/1985 | Krumkalns | 514/357 |
| 4,849,434 | 7/1989 | Enomoto et al. | 514/342 |

FOREIGN PATENT DOCUMENTS

| | | | |
|---|---|---|---|
| 0004129 | 9/1979 | European Pat. Off. | 71/94 |
| 0010420 | 4/1980 | European Pat. Off. | 71/94 |
| 0050002 | 4/1982 | European Pat. Off. | 548/204 |
| 0091148 | 10/1983 | European Pat. Off. | 514/369 |
| 0097323 | 1/1984 | European Pat. Off. | 546/280 |
| 0256687 | 2/1988 | European Pat. Off. | 546/280 |
| 0292305 | 11/1988 | European Pat. Off. | 546/280 |
| 48-17276 | 5/1973 | Japan | 546/280 |
| 57-85380 | 5/1982 | Japan | 548/204 |
| 57-88170 | 6/1982 | Japan | 548/204 |
| 61-103881 | 5/1986 | Japan | 546/280 |

OTHER PUBLICATIONS

Chem. Abstracts, vol. 109(1), Abst. No. 6503q, Jul. 4, 1988.
Chem. Abstracts, vol. 107(7), Abst. No. 54190h, Aug. 17, 1987.
Chem. Abstracts, vol. 93(25), Abst. No. 239,437e, Dec. 22, 1980.
Chem. Abstracts, vol. 92(13), Abst. No. 110,995k, Mar. 31, 1980.
J.A.C.S., 75, 109–114 (1953), Pennington et al.
J.A.C.S., 76, 578–580 (1954), Surrey et al.
J.A.C.S., 70, 3436–3439 (1948), Troutman et al.
J. Indian Chem. Soc., vol. LIV, 1977, 765–768, Vakil.
J. Indian Chem. Soc., vol. LIII, 1976, 595–597, Singh.
J. Indian Chem. Soc., vol. LV, 1978, 424–426, Jadhav et al.
J. Biol. Chem., 255, 5514–5516 (1980), Hanahan et al.

*Primary Examiner*—Alan L. Rotman
*Attorney, Agent, or Firm*—Stevens, Davis, Miller & Mosher

[57] ABSTRACT

A 2-pyridyl-thiazolidin-4-one derivative represented by the formula:

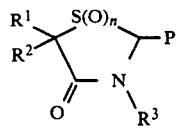

wherein $R_1$ and $R_2$ are each a hydrogen atom, an $C_1$–$C_{20}$ alkyl group, an $C_2$–$C_{20}$ alkenyl group, an $C_2$–$C_{20}$ alkynyl group, an aryl group, a $C_3$–$C_8$ cycloalkyl group or an aralkyl group which may have a substituent, $R_3$ is a hydrogen atom, an $C_1$–$C_{20}$ alkyl group, an $C_2$–$C_{20}$ alkenyl group, an $C_2$–$C_{20}$ alkynyl group, a $C_3$–$C_8$ cycloalkyl group or an aralkyl group which may have a substituent, P is a pyridyl group or its N-substituted pyridinium salt which may have a substituent, said substituent being selected from the group consisting of halogen atom, cyano group, hydroxy group, amino group, lower alkyl group, lower alkoxy group, lower alkylamino group, halogenated lower alkyl group, acyl group, acyloxy group, acylthio group, acylamino group, carboxyl group, lower alkoxycarbonyl group, carbamoyl group, lower alkyl substituted carbamoyl group, heterocyclic group, and lower cycloalkyl group, and n represents an integer of 0, 1 or 2, or a pharmaceutically acceptable salts thereof and an antiulcer agent which contains, as an effective ingredient, said 2-pyridyl-thiazolidine-4-one derivative or a pharmaceutically acceptable salt thereof.

6 Claims, No Drawings

CERTAIN PYRIDYL-THIAZOLIDIN-4-ONE HAVING ANTI-ULCER ACTIVITY

BACKGROUND OF THE INVENTION

1. Field of the Invention

The present invention relates to a 2-pyridyl-4-thiazolidinone derivative and a pharmacologically acceptable salt thereof which exhibit remarkable antiulcer effect in experimental ulcer, especially stress-induced ulcer and are useful as medicines for treatment of gastric and duodenal ulcers of mammals including humans.

2. Description of the Prior Art

Hitherto, for treatment of gastric and duodenal ulcers, many medicines have been developed and used, for example:

(1) Gastric antacids and pepsin inhibitor which neutralize and inactive gastric juice.

(2) Anticholinergic agent and histamine $H_2$-receptor antagonist which inhibit secretion of gastric juice by antagonizing acetylcholine and histamine which are chemical transmitters of participating in gastric acid secretory mechanisms.

(3) Medicines which activate gastric muscosal defensive mechanisms and accelerate repair process of a damaged gastric mucosa.

Furthermore, recently the following medicines have been studies for development and application to antiulcer medicines and some of them have been put on the market.

(4) Medicines which utilize gastric acid inhibitory action or cytoprotective action of prostaglandins.

(5) Medicines which show anti-secretory action and anti-ulcer action owing to $H^+$, $K^+$-ATPase inhibition (proton pump inhibitors).

However, there have not yet been developed anti-secretory and anti-ulcer medicines which act on central nervous system (CNS) and/or nervous system which transmits stimulus from CNS (hereinafter referred to as "Centrally acting inhibitory effect of gastric acid secretion or centrally acting gastric acid inhibitory effect").

These medicines having such effects are thought to be effective for treatment of recently increasing gastric and duodenal ulcers caused by stress.

The following seven reports have been made on study of 2-pyridylthiazolidine-4-one derivatives which are aimed at by the present invention.

That is, N-(substituted or unsubstituted phenyl and pyridyl) derivatives having uses as agricultural chemicals reported in Japanese Patent Kokai No. 54-145670; compounds including mainly N-(substituted or unsubstituted phenyl, benzyl and cycloalkyl) derivatives having uses as agricultural chemicals in Japanese Patent Kokai No. 55-55184; N-(carboxycyclohexylmethyl) derivatives having anticomplementary and N-(carboxymethylphenyl) derivatives having anti-inflammatory, analgesic and antirheumatic activity in Japanese Patent Kokai Nos. 57-85380 and 57-88170, respectively; N-(pyrazinyl) derivatives having uses as agricultural chemicals in Japanese Patent Kokai No. 58-183689; N-(substituted phenyl) derivatives having uses as intermediates in synthesis in U.S. Pat. No. 4,501,746; and N-(substituted carbamoyloxy) derivatives having a use as a cardiac in Japanese Patent Kokai No. 61-103881.

As mentioned above, not a few of 2-pyridylthiazolidin-4-one derivatives have excellent pharmacological action, but there has been made no report that they have any inhibitory effect of gastric acid secretion and anti-ulcer activity. Among the compounds having thiazolidin-4-one skeleton, Japanese Patent Kokai No. 57-64683 discloses that 2-substituted phenyl-5-alkylthiazolidin-4-one compounds have an effect as an antipeptic ulcer medicine.

However, none of these publications disclose that the compounds act on central nervous system and/or nervous system transmitting stimulus from central nervous system, resulting in remarkable central nervous type anti-secretory action and antiulcer action which are aimed at by the present invention.

As described hereinafter in Examples 2-(3,4-dimethoxyphenyl)-5-methylthiazolidin-4-one (Mezolidon) disclosed in the above Japanese Patent Kokai No. 57-64683 was evaluated by the test method employed in the present invention to find that this compound had extremely low effect as compared with the compound of the present invention and was nearly ineffective.

Medicines which are used for remedy of gastric and duodenal ulcers at present are roughly classified into (1) those which inhibit gastric acid secretion such as anticholinergic agent and $H_2$ antagonist, (2) those which neutralize and inactive secreted digestive fluid such as antacid and pepsin inhibitor and (3) those which activate defensive function of gastric and duodenal muscosae against digestive fluid. These medicines all act at peripheral level where gastric acid is secreted or digestion is effected and exhibit curative effect of ulcer by direct affection on the function of alimentary tract.

However, the functions of gastric secretion, gastro-duodenal motility and mucosal blood flow are all controlled by brain and it is considered that irregularity in the regulation by brain due to stress or the like will cause ulceration. That is, emission of abnormal stimulus from brain due to stress or the like induces acceleration of gastric acid secretion or gastric motility through excitation of vagus nerve and reduction of mucosal blood flow through excitation of splanchnic nerve, resulting in self digestion of gastric walls.

In other words, as causes of peptic ulcer, not only part of the peripheral nervous system, but also that of the central nervous system are important. Especially, for humans, mental and physical stress is considered to give a great effect on occurrence, retention and recurrence of ulcer and ulcer is considered to be one of psychological diseases. Therefore, if irregularity of central regulation for alimentary tract functions such as gastric acid secretion which has been caused by stress can be improved, this is expected to be an effective therapy of ulcer.

However, there have been substantially no medicines which act on central nervous system or nervous system which transmits stimulus from central nervous system to exhibit anti-secretory effect and anticulcer effect. Therefore, in actual treatment of ulcer, mostly ordinary anticulcer medicine is used in combination with antianxiety medicine, tranquillizer or the like. However, these medicines are not selective for central regulatory mechanisms of gastric acid secretion and have depressive effect on central nervous system, so they often cause side-effects such as drowsiness and hypoactivity.

SUMMARY OF THE INVENTION

The object of the present invention is to provide a 2-pyridyl-4-thiazolidinone derivative which is effective for treatment of gastric and duodenal ulcers which acts on central nervous system and/or nervous system transmitting the stimulus from central nervous system to exhibit central nervous type anti-secretory effect and antiulcer effect and which is free from the side-effects as mentioned above.

The inventors have made intensive researches in an attempt to develop medicines which exhibit remarkable anti-secretory effect and antiulceration effect by acting on central nervous system and/or nervous system transmitting stimulus from central nervous system and thus which are effective for treatment of peptic-ulcers such as gastric and duodenal ulcers caused by stress or the like.

As a result, it has been found that 2-pyridylthiazolidin-4-one derivatives represented by the formula (I):

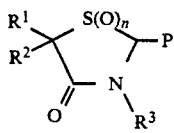

(wherein $R^1$, $R^2$ and $R^3$ each represents hydrogen, an alkyl group of $C_1$-$C_{20}$, an alkenyl group of $C_2$-$C_{20}$, an alkynyl group of $C_2$-$C_{20}$, an aryl group, a cycloalkyl group of $C_3$-$C_8$ or an aralkyl group and these groups may have a substituent selected from the group consisting of halogen atom, cyano group, hydroxy group, amino group, lower alkyl group, lower alkoxy group, lower alkylamino group, halogenated lower alkyl group, acyl group, acyloxy group, acylthio group, acylamino group, carboxyl group, lower alkoxycarbonyl group, carbamoyl group, lower alkyl substituted carbamoyl group, heterocyclic group, and lower cycloalkyl group, P represents a pyridyl group or a substituted pyridyl group and n represents an integer of 0, 1 or 2, or salts thereof exhibit substantially no inhibitory action for peripheral nerve type acid secretion induced by histamine or bethanechol, but show conspicuous inhibitory effect on central nerve type acid secretion induced by baclofen or TRH (thyrotropin-releating hormone) and thus exhibit antiulcer action. The present invention is based on this finding. That is, this shows that the compounds of the present invention are medicines which act on central nervous system and/or nervous system transmitting stimulus from central nervous system to cause inhibition of secretion of gastric acid and exhibit antiulceration action.

It is considered that there is the possibility that some of gastric ulcer and duodenal ulcer seen in models of climinal test and animal test may be caused by PAF (platelet activating factor). However, as shown by test examples referred to hereinafter, the central nervous type antiulceration action exhibited by the compounds of the present invention is essentially completely different from that induced by anti-PAF action and it is clear that such action cannot be expected from anti-PAF action.

DETAILED DESCRIPTION OF THE INVENTION

Various groups in the formula (I) included in the scope of the present invention are exemplified below.

The halogen means chlorine, bromine, iodine and fluorine. The lower alkyl means lower alkyl groups of 1-6 carbon atoms such as methyl, ethyl, n-propyl, isopropyl, butyl, isobutyl, tert-butyl, pentyl, and hexyl, preferably lower alkyl groups of 1-4 carbon atoms such as methyl, ethyl, n-propyl, isopropyl, butyl, isobutyl, and tert-butyl, and more preferably lower alkyl groups of 1-3 carbon atoms such as methyl, ethyl, n-propyl and isopropyl.

Lower alkyl portion in the lower alkoxy has the same meanings as defined above for the lower alkyl group and the lower alkoxy is preferably methoxy, ethoxy, n-propoxy and isopropoxy.

Lower alkyl in the lower alkylamino also has the same meanings as defined above for the lower alkyl and the alkylamino is in the form of mono- or di-substitution and preferred are methylamino, dimethylamino, ethylmethylamino, ethylamino, diethylamino, propylamino, dipropylamino and ethylpropylamino.

The halogenated lower alkyl means the above-mentioned lower alkyls containing the above-mentioned halogens. Preferred are methyl, ethyl, n-propyl and isopropyl substituted with the above-mentioned halogens and more preferred are methyl, ethyl, n-propyl and isopropyl having at least one chlorine or fluorine.

The acyl and acyl in acyloxy, acylthio and acylamino mean alkanoyls of 1-6 carbon atoms such as, for example, formyl, acetyl, propionyl, butyryl, isobutyryl, valeryl, isovaleryl, oxalyl, succinyl, pivaloyl and hexanoyl: alkoxycarbonyls of 1-6 carbon atoms such as, for example, methoxycarbonyl, ethoxycarbonyl, propoxycarbonyl, isopropoxycarbonyl, botoxycarbonyl, tert-butoxycarbonyl, pentyloxycarbonyl, tert-pentyloxycarbonyl and hexyloxycarbonyl; aralkoxycarbonyl such as for example, benzyloxycarbonyl and phenetyloxycarbonyl; aroyls such as benzoyl and toluoyl; alkanesulfonyls of 1-6 carbon atoms such as, for example, mesyl, ethanesulfonyl, 1-methylethanesulfonyl, propanesulfonyl and butanesulfonyl; and arenesulfonyls such as, for example, benzenesulfonyl, docyl and naphthalenesulfonyl. Among them, preferred are formyl, acetyl, butyryl, isobutyryl, benzoyl and mesyl.

The lower alkyl portion in the lower alkoxycarbonyl has the same meanings as the above-mentioned lower alkyl and preferred examples of the lower alkoxycarbonyl are methoxycarbonyl, ethoxycarbonyl, n-propoxycarbonyl, isopropoxycarbonyl and tert-butoxycarbonyl.

The lower alkyl substituted carbamoyl means carbamoyls where hydrogen attached to nitrogen atom is substituted with the above-mentioned lower alkyl and examples thereof are methylcarbamoyl, dimethylcarbamoyl, ethylcarbamoyl, diethylcarbamoyl, ethylmethylcarbamoyl, propylcarbamoyl and dipropylcarbamoyl.

The heterocyclic group means cyclic groups of 1-6 carbon atoms which contain at least one nitrogen atom, oxygen atom or sulfur atom in the ring and may contain at least one double bond in the ring. Preferred are pyrrolidinyl, piperidinyl, homopiperidinyl, morpholinyl, piperadinyl, N-methylpiperadinyl, pyrrole, imidazole, pyrazole, thienyl, thiazole, oxaxole, aminothiazole and furyl.

The lower cycloalkyl means cyclic hydrocarbon groups and examples thereof are substituted or unsubstituted cycloalkyls such as, for example, cyclopropyl, cyclobutyl, cyclopentyl, cyclohexyl, cycloheptyl, cyclooctyl and 1-methylcyclohexyl.

The alkyl group of $C_1$-$C_{20}$ means alkyls of 1-20 carbon atoms and examples thereof are straight chain and branched alkyl groups such as methyl, ethyl, n-propyl, n-butyl, sec-butyl, n-pentyl, iso-pentyl, n-hexyl, n-heptyl, n-octyl, n-nonyl, n-decyl, n-undecyl, n-dodecyl, tridecyl, tetradecyl, pentadecyl, hexadecyl, heptadecyl, octadecyl, nonadecyl and eicosanyl.

The alkenyl of $C_2$-$C_{20}$ means the above-mentioned alkyls of $C_1$-$C_{20}$ which have double bond at least one position of alkyl chain of two or more carbon atoms ($C_2$-$C_{20}$). Examples thereof are straight chain and branched alkenyls such as vinyl, 2-propenyl, 2-butenyl, 3-methyl-2-butenyl, 2-pentenyl, 3-pentenyl, 4-pentenyl, 4-methyl-3-pentenyl, 2-hexenyl, 4-hexenyl, 5-methyl-4-hexenyl, 2-heptenyl, 6-methyl-5-heptenyl, 2-heptenyl, 2-octenyl and 6-octenyl.

The alkynyl of $C_2$-$C_{20}$ means the above-mentioned alkylnyls of $C_2$-$C_{20}$ which have triple bond in place of the double bond.

The aryl means substituted and unsubstituted phenyl and naphthyl.

The cycloalkyl of $C_3$-$C_8$ means cyclic hydrocarbon groups, for example, substituted and unsubstituted cycloalkyl groups such as cyclopropyl, cyclobutyl, cyclopentyl, cyclohexyl, cycloheptyl and 1-methylcyclohexyl.

The aralkyl means groups composed of the above mentioned alkyl of $C_1$-$C_{20}$ and the above-mentioned aryl which are bonded through single bond. Examples are benxyl, 1-phenylethyl, 2-phenylethyl and naphthylmethyl.

The pyridyl group or substituted pyridyl represented by P may bond through any of 1-4 positions of the pyridine ring to the thiazolidin-4-one structure.

The substituted pyridine means pyridyls which have substituent as defined above on the position with exception of bound site to the thiazolidin-4-one structure and N-substituted pyridinium salt. Examples are 2-methylpyridyl, 6-methylpyridyl, 2-chloropyridyl, 6-chloropyridyl, 2-fluoropyridyl, 6-fluoropyridyl, N-methylpyridyl.

Salts of 2-pyridyl-thiazolidin-4-one derivatives represented by the formula [I] may be any of pharmaceutically acceptable salts and as examples thereof, mention may be made of salts with inorganic acids and organic acids, for example, salts with mineral acids such as hydrochloric acid, hydrobromic acid, sulfuric acid and phosphoric acid; salts with organic carboxylic acids such as formic acid, acetic acid, fumaric acid, maleic acid, citric acid, lactic acid, malic acid, tartaric acid, and aspartic acid; and salts with sulfonic acids such as methanesulfonic acid, benzenesulfonic acid, toluenesulfonic acid, hydroxybenzenesulfonic acid, dihydroxybenzenesulfonic acid and naphthalenesulfonic acid.

The compounds of the present invention include optical isomers and geometrical isomers and furthermore, include all hydrates, solvates and crystal forms.

The 2-pyridyl-thiazolidin-4-one derivatives represented by the formula [I] can be prepared, for example, by the following methods.

A sulfide derivative [I] (n=0) which is an objective compound of the present invention can be prepared by the following method and, if necessary, various substituents may be introduced therein or may be changed to other substituents as shown in the Examples hereinafter by methods known in synthetic organic chemistry.

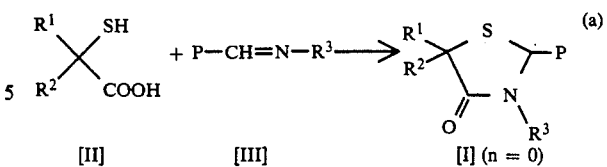

(wherein $R^1$, $R^2$, $R^3$ and P are as defined hereinbefore).

The present compound [I] (n=0) can be prepared by subjecting thioglycolic acid derivative [II] and Schiff's base [III] to ring closure in an inert solvent. The organic solvent includes general inert solvents used for dehydration reaction such as benzene, toluene, xylene, methylene chloride, 1,2-dichloroethane, chloroform, and tetrahydrofuran and mixtures of these solvents with ethanol and the like. The reaction can be effected at a temperature of from 20° C. to a refluxing temperature. It is preferred to carry out the reaction at refluxing temperature with azeotropic dehydration.

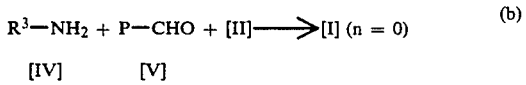

(wherein $R^3$ and P are as defined hereinbefore).

That is, compound [I] (n=0) can be prepared by subjecting primary amine [IV], compound [II] and aldehyde [V] to ring closure in an inert solvent. As organic solvents, there may be used common inert solvents used for dehydration reaction such as benzene, toluene, xylene, methylene chloride, 1,2-dichloroethane, chloroform and tetrahydrofuran and mixtures of these solvents with ethanol and the like. The reaction can be carried out at from 20° C. to refluxing temperature. It is preferred to promote the reaction by carrying out the reaction at refluxing temperature with azeotropic dehydration.

Furthermore, a sulfoxide derivative [I] (n=1) which is an objective compound can be prepared by subjecting the compound [I] (n=0) to oxidation reaction. Oxidizing agents used here include, for example, peracids such as m-chloroperbenzoic acid, peracetic acid, trifluoroperacetic acid, and permaleic acid, hydrogen peroxide, sodium bromite and sodium hypochlorite. As solvents used in the reaction, mention may be made of, for example, halogenated hydrocarbons such as chloroform and dichloromethane, ethers such as tetrahydrofuran and dioxane, amides such as dimethylformamide, alcohols such as ethanol, isopropanol and t-butanol and water, these may be used alone or in combination of two or more. Further, there may be used catalysts such as vanadium pentoxide and tungstic acid. The oxidizing agent may be used suitably in an substantially equivalent or somewhat excess amount for the compound [I] (n=0), namely, about 1-3 equivalents, more preferably about 1-1.5 equivalent. The reaction may be carried out at from a temperature of cooling with ice to about boiling point of solvent used, normally at from a temperature of cooling with ice to room temperature and more preferably from about 0° C. to 10° C. Reaction time is normally about 0.1-24 hours, more preferably about 0.1-4 hours.

A sulfone derivative [I] (n=2) which is an objective compound in the present invention can be prepared by subjecting the compound [I] (n=0) or the compound [I] (n=1) to oxidation reaction. The oxidizing agents, solvents, catalysts and reaction conditions used in preparation of compound [I] (n=1) can be used for this oxidation reaction, but amount of the oxidizing agent is suitably about 2 equivalents to a largely excess amount for compound [I] (n=0) and about an equivalent to a largely excess amount for compound [I] (n=1). The largely excess amount is preferably 6-10 equivalents.

The compound [I] (n=0) is useful as a starting compound for preparing compounds [I] (n=1 and 2).

The present compound represented by the formula [I] and salts thereof can be administered orally or parenterally when used as medicines. That is, they can be orally administered in ordinary dosage forms such as tablets, capsules, sirups, suspensions and solutions or parenterally in the form of injectable liquid such as solutions, emulsions and suspensions. Furthermore, they can be administered rectally in suppository form or in the form of inharation spray or percutaneous agents.

The above-mentioned suitable dosage forms can be prepared by adding the present effective compound to normally acceptable carriers, excipients, binders, stabilizers, etc. For use in the form of injections, it is possible to add acceptable buffers, solubilizing aids, isotonic agents, etc. to the present compound.

Dosage and frequency of administration vary depending on condition, age, and weight of patient and dosage form, but normally about 1-5000 mg, preferably 10-2000 mg once or in parts in several times a day for an adult.

The following nonlimiting examples will further explain the present invention.

TEST METHOD

Sprague-Dawley strain male rats (body weight: 200-250 g) fasted for 24 hours (with free access of water) were used for the test.

(1) Antiulcer test

Anticular effect of the compound was examined by means of water-immersion and restraint stress induced gastric ulcer model in rats.

The ulcer experiment was performed in accordance with the method of Takagi and Okabe referred to hereinafter.

Rats were immobilized in a restraint cage. The animals were then immersed vertically to the level of the xiphoid process in water bath (23° C.) for 17 hr and killed by deep ether anesthesia.

The stomach of each rat was removed and inflated by injecting 10 ml of 1% formalin to fix the inner and outer layer of gastric wall.

Subsequently, the stomach was incised along the greater curveture and the length of ulcers in glandular portion was measured.

The sum of the length (mm) of each ulcer was used as an ulcer index.

Test compound was suspended in 0.5% methylcellulose solution and was orally administered at a volume of 5 ml/kg to the rat 30 minutes prior to stress loading. To the control group was administered vehicle alone at the same volume. Inhibitory percentage of ulcer formation of the compound was calculated from the following formula.

$$\frac{\text{Ulcer index of control group} - \text{ulcer index of treated group}}{\text{Ulcer index of control group}} \times 100$$

Method of Takagi, K. and Okabe, S.: Japan. J. Pharmacol., 18, 9-18 (1968)

| (Inhibitory percentage) | (Judgement) |
| --- | --- |
| Less than 40%. | − |
| Not less than 40% and less than 60%. | + |
| Not less than 60% and less than 80%. | ++ |
| Not less than 80%. | +++ |

| Compound (Example No.) | Dose (mg/kg) | Effect |
| --- | --- | --- |
| 1 | 50 | ++ |
| 2 (Isomer II) | 50 | +++ |
| 30 | 50 | + |
| 31 | 50 | ++ |
| 33 | 30 | +++ |
| 34 | 100 | ++ |
| 42 | 50 | +++ |
| 46 | 50 | ++ |
| 48 | 50 | + |
| 52 | 50 | + |
| 178 | 100 | + |
| 198 | 100 | +++ |
| 199 | 100 | +++ |
| 221 | 100 | +++ |
| 246 | 100 | ++ |
| 274 | 100 | +++ |
| Mezolidon (Compound of Japanese Patent Kokai No. 57-64683) | 100 | − |
| Cimetidine | 30 | ++ |

(2) Test on central acting inhibitory effect of gastric acid secretion

Whether the antisecretory effect of the compound is based on central action or not was judged according to mode of antisecretory action of the compound to centrally stimulated gastric acid secretion and peripherally stimulated gastric acid secretion. That is, if the antisecretory action of the compound is based on peripheral action, both the gastric acid secretion stimulated peripherally (e.g. by the administration of histamine or bethanechol) and the gastric acid secretion stimulated centrally (e.g. by the administration of baclofen) are inhibited, but if it is based on central action, only the centrally stimulated acid secretion is inhibited and the peripherally stimulated acid secretion is not inhibited.

We determined the site of action (central or peripheral) of the compound by the result from above examination.

Rat was fasted for 24 hours and then cervical portion was cut open under urethane anestesia (1.2 g/kg i.p.) and a tracheal cannula was inserted therein. Two soft silicone cannulas were inserted into the gastric lumen through an esophagus and a pyrolus resectively.

The esophagus and pylorus were ligated to fix the cannulas and the gastric lumen was gently rinsed with saline before starting the experiment.

Gastric acid was collected every 20 min. by flushing the gastric lumen with 5 ml saline. The acid content of each sample was determined by titration of 0.02 N-NaOH.

Peripheral stimulation of gastric acid secretion was carried out by subcutaneous administration of 10 mg/kg of histamine or 1 mg/kg of bethanechol. Central stimulation of gastric acid secretion was performed by subcutaneous administration of 2 mg/kg of baclofen. The test compound was suspended in 0.5% methylcellulose solution and was administered into duodenum 2 hours before administration of stimulant. Inhibitory percentage of acid secretion of the compound was calculated from the following formula.

$$\frac{\text{Acid output of control group} - \text{Acid output of treated group}}{\text{Acid output of control group}} \times 100$$

Statistical analysis

Student's t-test was used to determine the statistical significance of the data and $P < 0.05$ was regarded as significant.

| (Inhibitory percentage) | (Judgement) |
| --- | --- |
| Less than 40%. | — |
| Not less than 40% and less than 60%. | + |
| Not less than 60% and less than 80%. | ++ |
| Not less than 80%. | +++ |

| Compound (Example No.) | Stimulant | | | Dose (Route of administration) |
| --- | --- | --- | --- | --- |
| | Baclofen | Histamine | Bethanechol | |
| 2 (isomer II) | +++ | — | — | 30 mg/kg (Administration into duodenum) |

(3) Test on PAF-induced ulcer

Inhibitory effect of the compound on PAF-induced ulcer was examined. PAF-induced ulcer in rat was caused by intravenous administration of 10 μg/kg of PAF. One hour after PAF administration, rat was killed under deep ether anesthesia and stomach was removed. The stomach was inflated and fixed by injecting 10 ml of 1% formalin solution and then cut open along greater curvature. Areas (mm$^2$) of the ulcerated portions were measured and sum of them was taken as ulcer-index. Test compound was suspended in a 0.5% methylcellulose solution and orally administered at a volume of 5 ml/kg 30 minutes before the administration of PAF. Vehicle alone was administered to control rat at the same volume with test group. With reference to the effect of the compound to inhibit ulceration, results of treated group and those of control group were compared and those which have a statistical significance was judged to be effective.

| Compound (100 mg/kg P.O.) | Anti-PAF[b] test in vitro (IC$_{50}$ μg/ml) | Effects at administration of 100 mg/kg P.O. | |
| --- | --- | --- | --- |
| | | Test on inhibition of PAF-induced ulcer Test (3) | Test on anti-ulceration (ulcer caused by stress) Test (1) |
| Example | | | |
| No. 1 | 5.8 | Effective | Effective |
| No. 42 | 4.0 | Effective | Effective |
| L-652731[a] (Compound of Japanese Patent Kokai No. 60-116679) | 0.2 | Effective | Ineffective |
| Cimetidine | | Ineffective (*) | Effective |

(*) Nature 319, 54–56 (1986)
[a] Compound described in page 595 (trans-2,5-bis(3,4,5-trimethoxyphenyl)tetrahydrofuran).
[b] Anti-PAF test in vitro (inhibitory action on platelet aggregation).

The inhibition of PAF-induced platelet aggregation was examined by using a platelet-rich plasma (PRP) of rabbit according to the method of Mustard et al. [J. F. Mustard et al., J. Lab. Blin. Med., 64, 548 (1964)], which is an improved method of Born [G.V.R. Born, J. Physiol., London, 162, 67 (1962)]. That is, 80–100 ml of blood per animal was collected from carotoid arteries of conscious male Japanese white rabbits into a polyethylene vessel containing 1/10 the volume of a 3.8% sodium citrate solution. A portion (about 3 ml) of the collected blood was centrifuged at a high speed (11,000 rpm) for 60 seconds to give a platelet-poor plasma (PPP) as supernatant. The remainder of the blood was centrifuged at a low speed (1000 rpm) for 10 minutes to give a platelet-rich plasma (PRP) as supernatant.

The degree of platelet aggregation was determined by nephelometry with an aggregometer (Hematracer, Niko Biosciene Co.) while stirring the PRP at 1000 rpm at 37° C. The degree of platelet aggregation was expressed in terms of the light transmittance (%), the value of PRP being taken as 0% and the value of PRP as 100%. A portion (0.2 ml) of the PRP was placed into a glass cuvette containing a silicone-coated stirring iron bar, and 2 μl of dimethylsulfoxide was added. After 2 minutes, PAF dissolved in physiological saline containing 0.25% BSA was added to give a final PAF concentration of 0.005 μg/μl, and the maximum aggregation was determined. To measure the inhibitory activity of test compounds on the platelet aggregation induced by PAF, 2 μl of a dimethylsulfoxide solution of each test compound was added in place of dimethylsulfoxide. The inhibitory percentage by the test compound of PAF-induced platelet aggregation was calculated according to the following equation and the value of IC$_{50}$ was determined.

$$\text{Inhibitory percentage} = \left[ 1 - \frac{\text{Max. aggregation in the presence of test compound}}{\text{Max. aggregation in the absence of test compound}} \right] \times 100$$

As mentioned hereinabove, the present compound exhibits strong anti-ulcer action by selective inhibition of central regulatory mechanisms of acid secretion, in other words, by suppressing gastric acid secretion stimulated by mental and physical stress.

A patent application was filed on a part of the present compound as anti-PAF agent in which treatment of gastric and duodenal ulcers induced by PAF was included as uses of the compound. However, it is considered that ulcers induced by PAF are limited to extremely special cases (ulcers) and the general anti-ulcer action as shown here is essentially utterly different from PAF-induced ulcer inhibitory action.

Differences between stress ulcer induced by psychological factors and the PAF-induced ulcer will be specifically explained below.

The stress ulcer is due to self digestion of walls of stomach which is caused by acceleration of aggressive factors (e.g., acid secretion) and simultaneous decrease of defensive factors caused by lowering of blood flow of gastric mucosa by recieving stress. On the other hand, PAF-induced ulcer has no relation with gastric acid and is considered to be caused solely by so-called vascular shock such as stasis of blood flow due to platelet aggregating action of PAF and increment of vascular permeability due to vasoactive amines released by PAF.

The difference between these two ulcers can also be clearly admitted by visual observation. That is, the ulcer caused by stress is brown and linear necrosis like other many experimental ulcers while the PAF-induced ulcer is widely extending and bright red in color.

As explained above, the stress-induced ulcer and the PAF-induced ulcer are of clearly different type from both the cause and the visual observation.

Pathological and physiological role of PAF is at present considered to be a mediator for shock, allergy and inflammation. From this viewpoint, there is the possibility of PAF participating in special cases of peptic ulcers induced by traumatic shocks such as burns and fracture of a bone. That is, it is considered that clinically anti-ulcer agent based on anti-PAF action is used for treatment of gastrointestinal hemorrhage and ulceration caused by shock in emergency cases due to burning, traffic accidents, etc. On the other hand, the effect of the present invention is based on anticular action due to inhibition of acid secretion and so, the present compound can be used for treatment of general peptic ulcers which are not induced by PAF, like other anti-secretory and/or anticular agents (for example, cimetidine, pirenzepine, etc.). In this respect, the two are greatly different.

This is also clear by comparison of drug effect on PAF-induced ulcer and on stress-induced ulcer which is one of general ulcers. That is, PAF-induced ulcer cannot be inhibited by commonly used anti-secretory and/or anti-ulcer agents such as Cimetidine, but remarkably inhibited by anti-PAF agents such as L-652731. On the other hand, stress-induced ulcer which is often employed as a model of general ulcers for test on effect of anti-ulcer agents can be inhibited by Cimetidine, but cannot be inhibited by L-652731 which is an authentic anti-PAF agent. Thus, the PAF-induced ulcer is considered to be classified as a special ulcer also from the aspect of effect of medicines thereon. The compounds sown in the present invention are utterly different from anti-ulcer agents based on anti-PAF action in that they have strong effect on stress-induced ulcer on which anti-PAF agent is ineffective and can be widely applied to general peptic ulcers induced by clinically various causes.

REFERENCE EXAMPLE 1

Preparation of methyl-(4-chlorophenyl)-acetate

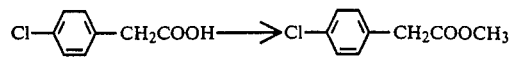

4-Chlorophenylacetic acid (100 g, 0.59 mol) was dissolved in 1,2-dichloroethane (165 ml) and methanol (96 ml, 2.4 moles) and to the solution was added concentrated sulfuric acid (2.75 ml), followed by refluxing for 6 hours. The mixture was cooled and aqueous NaHCO$_3$ was added, followed by stirring. The resulting organic layer was separated, dried over anhydrous sodium sulfate, collected by filtration and concentrated to dryness to obtain methyl-(4-chlorophenyl)-acetate (102 g, yield 94%).

NMR (CDCl$_3$) δppm: 3.60 (2H, s), 3.70 *(3H, s), 7.15–7.35 (4H, s).

REFERENCE EXAMPLE 2

Preparation of methyl-(4-chlorophenyl)-bromoacetate

Methyl-(4-chlorophenyl)-acetate (102 g, 0.55 mol) was dissolved in carbon tetrachloride (100 ml) and thereto was added N-bromosuccinimide (97.9 g, 0.55 mol). The mixture was refluxed and irradiated with 500W bromo lamp for 5 hours. Then, the mixture was cooled and filtered and the filtrate was concentrated to dryness to obtained methyl-(4-chlorophenyl)bromoacetate (150 g, yield 103%).

NMR (CDCl$_3$) δppm: 3.79 (3H, s), 5.31 (1H, s), 7.3–7.7 (4H, s).

REFERENCE EXAMPLE 3

Preparation of methyl-α-(4-chlorophenyl)-α-acetylthioacetate

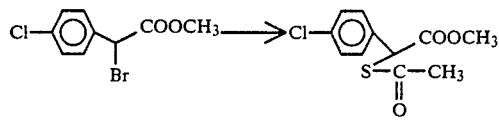

To 60% oily sodium hydride (22.0 g, 0.55 mol) was added dry dimethylformamide (300 ml) in a nitrogen atmosphere.

To the mixture was added dropwise thioacetic acid (46.0 g, 0.61 mol) at 0°–10° C., followed by keeping it for one hour at 0°–10° C. At 0°–10° C., thereto was added dropwise a solution prepared by dissolving methyl(4-chlorophenyl)bromoacetate (150 g, 0.55 mol) in dry dimethylformamide (200 ml) and then, this was kept for 1 hour at that temperature.

The reaction mixture to which 10% aqueous NaCl was added was extracted twice with benzene. The organic layer was washed with 5% aqueous NaHCl$_3$ and then twice with 10% aqueous sodium chloride solution, dried over anhydrous sodium sulfate and filtered. The filtrate was concentrated and the residue was purified by silica gel chromatography (5% ethyl acetate-hexane) to obtain methyl-α-(4-chlorophenyl)-α-acetylthioacetate (128.0 g, yield 95%).

NMR (CDCl$_3$) δppm: 2.35 (3H, s), 3.74 (3H, s), 5.28 (1H, s), 7.25–7.40 (4H, m).

REFERENCE EXAMPLE 4

Preparation of α-(4-chlorophenyl)-α-mercaptoacetic acid

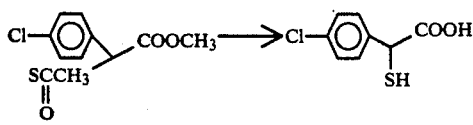

Methyl-α-(4-chlorophenyl)-α-acetylthioacetate (100 g, 0.39 mol) was dissolved in degased methanol (350 ml) and thereto was added a solution of sodium hydroxide (62.4 g, 1.56 mol) in degased water (150 ml), followed by refluxing for 5 hours. After cooled, 10% aqueous NaCl was added and the mixture was washed twice with hexane. The aqueous layer was adjusted to pH=1-2 with concentrated hydrochloric acid and extracted twice with benzene and the organic layer was washed with 10% aqueous NaCl, dried over anhydrous sodium sulfate and concentrated to dryness to obtain a-(4-chlorophenyl) α-mercaptoacetic acid (68 g, yield 86.8%).

NMR (CDCl$_3$) δppm: 2.62 (1H, d, J=7.6Hz), 4.67 (1H, d, J=7.6Hz), 7.3–7.45 (4H, s).

REFERENCE EXAMPLE 5

Preparation of N-nicotinylidenemethylamine

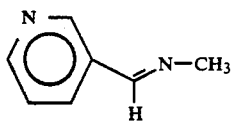

Nicotinaldehyde (10.7 g, 0.1 mol) was dissolved in toluene (100 ml) and thereto was added 40% aqueous methylamine solution (23.3 g, 0.3 mol) and the mixture was subjected to azeotropic dehydration for 3 hours. The reaction mixture was concentrated under reduced pressure to obtain N-nicotinylidenemethylamine (11.7 g).

NMR (CDCl$_3$) δppm: 3.53 (3H, d, J=1.7Hz), 7.3–8.85 (5H, m).

EXAMPLE 1

Preparation of 5-(4-chlorophenyl)-3-methyl-2-(3-pyridyl)thiazolidin-4-one

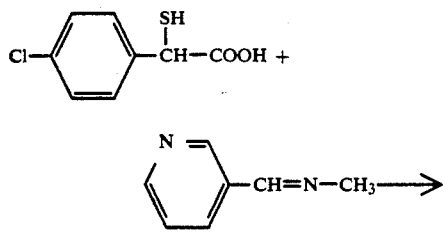

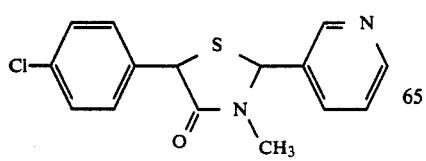

α-(4-Chlorophenyl)-60-mercaptoacetic acid (10.0 g, 0.049 mol) prepared in Reference Example 4 and N-nicotinylidenemethylamine (5.88 g, 0.049 mol) prepared in Reference Example 5 were dissolved in toluene (100 ml) and the solution was subjected to azeotropic dehydration for 2 hours. After cooled, the reaction mixture was washed with 5% aqueous NaHCl$_3$, dried over anhydrous sodium sulfate and filtered. The filtrate was concentrated under reduced pressure and the residue was purified by silica gel chromatography (5% acetone-chloroform) and recrystallized from ether to obtain 5-(4-chlorophenyl)-3-methyl-2(3-pyridyl)-thiazolidin-4-one (13.5 g, yield 90.0%). m.p. (100°–101.5° C.

EXAMPLE 2

5-(4-Chlorophenyl)-3-methyl-2-(3-pyridyl)-thiazolidin-4-one (3 g) obtained in Example 1 was purified by liquid chromatography [Lichroprep® Si-60 (40–63 μm), carrier; ethanol : hexane=1 : 9] to obtain isomer I and isomer II.

m.p. (isomer I): 140°–140.5° C.
m.p. (isomer II): 120°–120.5° C.

EXAMPLE 3

Preparation of 5-(4-chlorophenyl)-3-methyl-2-(3pyridyl)thiazolidin-4-one

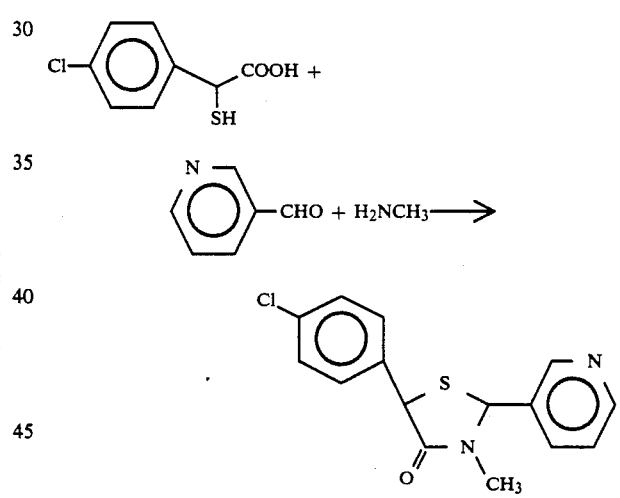

α-(4-Chlorophenyl)-α-mercaptoacetic acid (5.0 g, 0.025 mol) prepared in Reference Example 4, nicotinaldehyde (2.64 g, 0.025 mol) and 40% aqueous methylamine solution (5.75 g, 0.074 mol) were added to toluene (50 ml) and the mixture was subjected to azeotropic dehydration for 3 hours. After cooled, the mixture was concentrated under reduced pressure and the residue was purified by silica gel chromatography (5% acetone-chloroform) and then recrystallized from ether to obtain 5-(4-chlorophenyl)-3-methyl-2-(3-pyridyl)-thiazolidin-4-one (6.59 g, yield 87.6%). m.p. 100°–101.5° C.

Compounds of Examples 4–41 enumerated in Table 3 were obtained in the same manner as in Example 1 or 3.

REFERENCE EXAMPLE 6

Preparation of 2-mercaptoundecanoic acid (I) Methyl 2-bromoundecanoate $$n\text{-}C_{10}H_{21}COOH \rightarrow n\text{-}C_9H_{19}CHBrCOOCH_3$$

Undecanoic acid (100 g, 0.54 mol) was added to thionyl chloride (108 ml, 1.48 mol) and this mixture was refluxed for 2 hours. Then, bromine (29 ml, 0.57 mol) was added dropwise over 1.5 hours under reflux. Reflux was continued for 5 additional hours.

The resulting mixture was cooled to room temperature, methanol (250 ml, 6.1 mol) was added dropwise over 30 minutes, and this reaction mixture was left standing overnight. After addition of aqueous NaCl, the reaction mixture was extracted twice with ether. The extract was washed with aqueous NaHCO₃, aqueous Na₂SO₃, and aqueous NaCl, and then dried. The solvent was removed in vacuo, giving crude methyl 2-bromoundecanoate (145 g, 97% yield).

IR (neat) [cm⁻¹]; 2920, 2850, 1736, 1432, 1144

(II) Methyl 2-acetylthioundecanoate

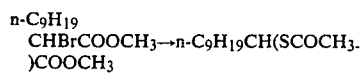

Dry dimethylformamide (600 ml) was added to 60% sodium hydride (22.5 g, 0.56 mol) under a stream of nitrogen. The mixture was cooled to 0° C., thioacetic acid (51.6 g, 0.68 mol) was added dropwise at 0° to 10° C., and the mixture was kept between those temperatures for 1 hour. Then crude methyl 2-bromoundecanoate (145 g, 0.52 mol) from above (I) was added dropwise at 0° to 10° C., and the mixture was kept between those temperatures for 2 hours. After addition of aqueous NaCl, the product mixture was extracted twice with ether. The extract was washed with aqueous NaHCO₃, aqueous Na₂SO₃, and aqueous NaCl, and dried. The solvent was removed in vacuo and the residue was purified by column chromatography, giving methyl 2-acetylthioundecanoate (108 g, 76% yield).

IR (neat) [cm⁻¹]; 2920, 2860, 1738, 1698, 1435, 1350, 1152, 950

(III) 2-Mercaptoundecanoic acid

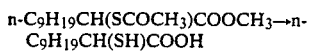

Methyl 2-acetylthioundecanoate (122.2 g, 0.44 mol) from above (II) was dissolved in methanol (527 ml). Water (226 ml) and NaOH (67.8 g, 1.67 mol) were added in turn. The mixture was heated under reflux for 2 hours and then cooled. After addition of water, the product mixture was extracted twice with hexane. The aqueous layer was acidified to a pH of 1 to 2 with conc. HCl, and extracted twice with ether. The combined extracts were washed with aqueous NaCl, and dried. The solvents were removed in vacuo, giving 2-mercaptoundecanoic acid (95.54 g, 98%

IR (CHCl₃) [cm⁻¹]; 2850, 1705

REFERENCE EXAMPLE 7

Preparation of N-nicotinylidene-N',N'-dimethylethylenediamine

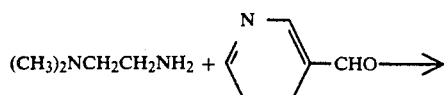

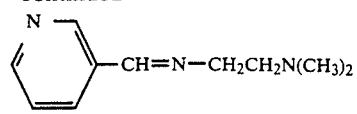

Nicotinealdehyde (2.16 ml, 22.9 mmol) and N,N-dimethylethylenediamine (2.51 ml, 22.9 mmol) were added to toluene (100 ml) and the mixture was subjected to azeotropic dehydration for 2 hours. After cooling, solvent was distilled off to obtain N-nicotinylidene-N',N'-dimethylethylenediamine (4.13 g, yield 102%).

NMR (δ, CDCl₃) ppm: 2.32 (6H, s), 2.66 (2H, t, J=6.8Hz) 3.78 (2H, t, J=6.8Hz), 7.25–8.86 (5H, m).

EXAMPLE 4

Preparation of 5-(n-nonyl)-2-(3-pyridyl)thiazolidin-4-one

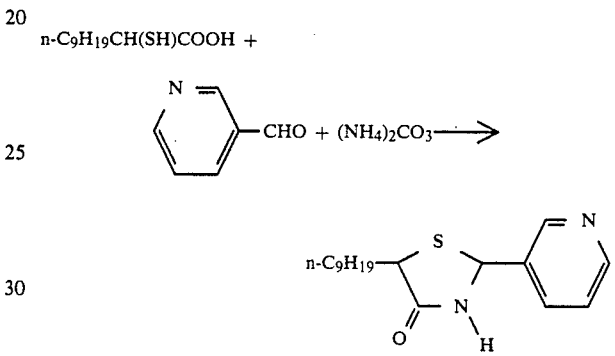

2-Mercaptoundecanoic acid (20 g, 91.6 mmol), nicotinaldehyde (8.64 ml, 91.6 mmol), and (NH₄)₂CO₃ (3 3 g, 34.3 mmol) were added to benzene (300 ml), and subjected to azeotropic dehydration for 2 hours. After the reaction mixture was cooled, (NH₄)₂CO₃ (3.3 g, 34.3 mmol) was added at 30°–40° C., and the mixture was subjected to azeotropic dehydration. Then the solvent was removed under reduced pressure. The residue was chromatographed on silica gel, and upon recrystallization from etherhexane, gave 5-(n-nonyl)-2-(3-pyridyl)-thiazolidin-4-one (16.7 g, 59% yield).

m.p. 90°–95° C.

Preparation of 3-(2-hydroxyethyl)-5-(n-nonyl)-2-(3-pyridyl)thiazolidin-4-one

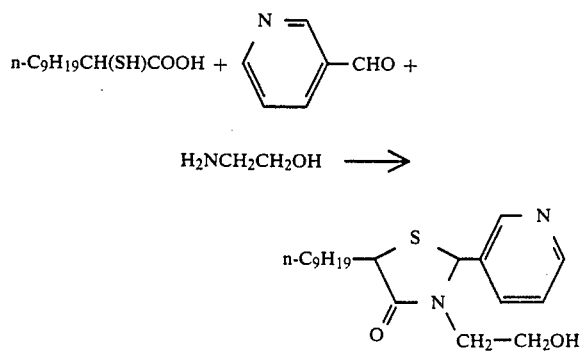

2-Mercaptoundecanoic acid (7 g, 32.1 mmol), nicotinaldehyde (3.03 ml, 32.1 mmol), and ethanolamine (1.93 ml, 32.1 mmol) were added to toluene (100 ml) and subjected to azeotropic dehydration for 1 hour. The product mixture was cooled and evaporated under reduced pressure to remove the solvent. The residue was purified by column chromatography, giving 3-(2-hydroxyethyl)-5-(n-nonyl)-2-(3-pyridyl)thiazolidin-4-one (8.17 g, 73% yield).

NMR (CDCl$_3$, δ) [ppm]; 0.85–0.9 (3H, m), 2.9–3.01 (1H, m), 3.65–3.80 (3H, m), 3.97–4.01 (0.7H, m), 4.02–4.07 (0.3H, m), 5.78 (0.3H, d, J=2.0Hz), 5.80 (0.7H, s).

Preparation of
3-(2-chloroethyl)-5-(n-nonyl)-2-(3-pyridyl)thiazolidin-4-one

Triphenylphosphine (3.44 g, 13 mmol) was added to a mixture of 3-(2-hydroxyethyl)-5-(n-nonyl)-2-(3-pyridyl)thiazolidin-4-one (3.49 g, 10 mmol) and carbon tetrachloride (20 ml) with stirring at room temperature. Then the mixture was refluxed with stirring for 2.5 hours. The product mixture was cooled and filtered to remove the formed crystals. The filtrate was concentrated and chromatographed, giving the cis-isomer (0.55 g) and trans-isomer (1.46 g) of the title compound and a mixture of two isomers (0.94 g) (total 2.95 g, 80% yield).

cis-Isomer
IR (CHCl$_3$) [cm$^{-1}$]; 2915, 2850, 1675, 1590, 1580, 1350
NMR (δ, CDCl$_3$, ppm); 2.99 (1H, ddd, J=14.52, 7.92 and 5.28Hz), 3.49 (1H, dt, J=11.55 and 5.28 Hz), 3.72 (1H, ddd, J=11.55, 7.92 and 5.28Hz), 3.95 (1H, dt, J=14.52 and 5.28Hz), 4.01 (1H, dd, J=9.90 and 2.97Hz), 5.86 (1H, s).

trans-isomer
IR (CHCl$_3$) [cm$^{-1}$]; 2920, 2850, 1678, 1590, 1580, 1355
NMR (δ, CDCl$_3$, ppm); 2.97 (1H, ddd, J=14.52, 8.24 and 4.95Hz), 3.51 (1H, ddd, J=11.54, 5.28 and 4.95Hz), 3.74 (1H, ddd, 11.54, 8.24 and 4.95Hz), 3.98 (1H, ddd, J=9.90, 3.63 and 1.64Hz), 5.85 (1H, d, J=1.64Hz).

EXAMPLE 7

Preparation of
3-(2-dimethylaminoethyl)-5-(n-nonyl)-2-3-pyridyl)-thiazolidin-4-one n-C$_9$H$_{19}$CH(SH)COOH +

2-Mercaptoundecanoic acid (2 g, 9.16 mmol) and N-nicotinylidene-N',N'-dimethylethylenediamine (1.62 g, 9.16 mmol) were dissolved in toluene (50 ml), and subjected to azeotropic dehydration for 2 hours. The solvent was removed from the product mixture by evaporation under reduced pressure The residue was purified by column chromatography, giving 3-(2-dimethylaminoethyl)-5-(n-nonyl)-2-(3-pyridyl)thiazolidin-4-one (3.1 g, 90% yield).

IR (CHCl$_3$) [cm$^{-1}$]; 2850, 1660, 1577, 1408

EXAMPLE 8

Preparation of
3-(2-dimethylaminoethyl)-5-(n-nonyl)-2-(3-pyridyl)-thiazolidin-4-one n-C$_9$H$_{19}$CH(SH)COOH +

2-Mercaptoundecanoic acid (5.0 g, 22.9 mmol), nicotinaldehyde (2.16 ml, 22.9 mmol), and N,N-dimethylethylenediamine (2.51 ml, 22.9 mmol) were dissolved in toluene (100 ml), and subjected to azeotropic dehydration for 2 hours. The solvent was removed from the product mixture by evaporation under reduced pressure. The residue was purified by column chromatography, giving -(2-dimethylaminoethyl)-5-(n-nonyl)-2-(3-pyridyl)thiazolidin-4-one (7.9 g, 91% yield).

IR (CHCl$_3$) [cm$^{-1}$]; 2850, 1660, 1577, 1408

EXAMPLE 9

Preparation of
5-ethyl-3-(2-dimethylaminoethyl)-2-(3-pyridyl)thiazolidin-4-one n-Butyllithium solution (5 ml, 8 mmol) in hexane was added dropwise to a solution of diisopropylamine (1.42 ml, 7.96 mmol) in dry tetrahydrofuran at −30° to −40° C. The mixture was kept between those temperatures for 1 hour and then cooled to −78° C. Thereto was added dropwise a solution of 3-(2-dimethylaminoethyl)-2-(3-pyridyl)thiazolidin-4-one (2 g, 7.96 mmol) in dry tetrahydrofuran (10 ml). This reaction mixture was kept at that temperature for 1 hour. Then, ethyl iodide (1.24 g, 7.96 mmol) was added, and this reaction mixture was slowly warmed up to room temperature and maintained there for 30 minutes. The resulting mixture, after addition of aqueous NaCl, was extracted with ethyl acetate. The extract was washed with aqueous NaCl, dried, and concentrated by evaporation under reduced pressure. The residue was purified by column chromatography, giving 5-ethyl-3-(2-dimethylaminoethyl)-2-(3-pyridyl)-thiazolidin-4-one (1.84 g, 83% yield).

NMR (CDCl$_3$, δ) [ppm]; 1.06 (3H, t, J=7.3Hz), 2.15 (6H, s), 3.75–3.85 (1H, m), 4.00–4.05 (1H, m), 5.86 (1H, d, J=2.0Hz)

EXAMPLE 10

Preparation of 5,5-dimethyl-3-(2-dimethylaminoethyl)-2-(3-pyridyl)-thiazolidin-4-one

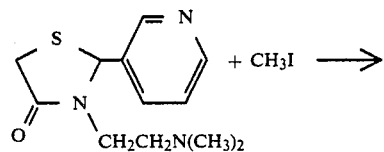

A n-butyllithium solution (10 ml, 16 mmol) in hexane was added to dropwise to a solution of diisopropylamine (2.84 ml, 15.9 mmol) in dry tetrahydrofuran (6 ml) at −20° to −30° C. The mixture was kept between those temperatures for 1 hour and then cooled to −78° C. Thereto was added dropwise a solution of 3-(2-dimethylaminoethyl)-2-(3-pyridyl)thiazolidin-4-one (2 g, 7.96 mmol) in dry tetrahydrofuran (10 ml). The resulting mixture was kept at −78° C. for 1 hour. After addition of methyl iodide (2.26 g, 15.9 mmol), this reaction mixture was slowly warmed up to the room temperature and allowed to stand overnight. The resulting mixture, after addition of aqueous NaCl, was extracted with ethyl acetate. The extract was washed with aqueous NaCl, dried, and the solvent was removed in vacuo. The residue was purified by column chromatography, giving 5,5-dimethyl-3-(2-dimethylaminoethyl)-2-(3-pyridyl)thiazolidin-4-one (257 mg, 12% yield).

m.p. 67°–70° C.

EXAMPLE 11

Preparation of 3-(2-dimethylaminoethyl)-5-(n-nonyl)-2-(3-pyridyl)-thiazolidin-4-one

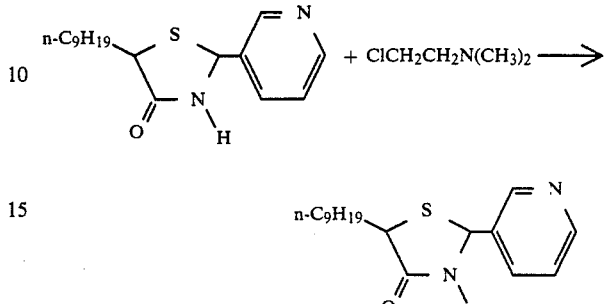

K$_2$CO$_3$ (0.9 g, 6.52 mmol) and 2-dimethylaminoethyl chloride hydrochloride (0.47 g, 3.26 mmol) were added to a solution of 5-(n-nonyl)-2-(3-pyridyl)thiazolidin-4-one (1 g, 3.26 mmol) in dry dimethylformamide (10 ml). The mixture was kept at 50° C. for 10 hours. The resulting mixture, after addition of aqueous NaCl, was extracted with ethyl acetate. The extract was washed with aqueous NaCl, dried, and the solvent was removed in vacuo. The residue was purified by chromatography on silica gel, giving 3-(2-dimethylaminoethyl)-5-(n-nonyl)-2-(3-pyridyl)thiazolidin-4-one (0.41 g, 0.41 g, 33% yield).

IR (CHCl$_3$) [cm$^{-1}$]; 2850, 1660, 1578, 1407

EXAMPLE 12

Preparation of 3-(2-acetylaminoethyl)-5-(n-nonyl)-2-(3-pyridyl)-thiazolidin-4-one

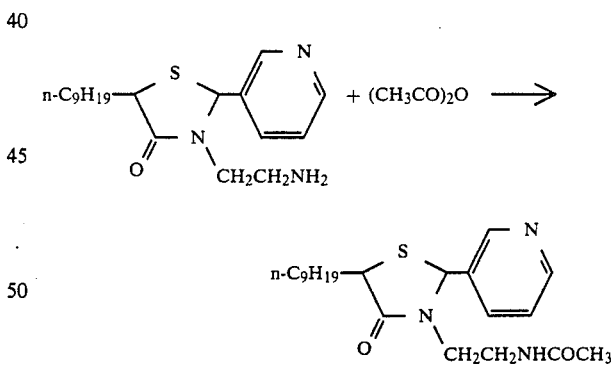

Acetic anhydride (0.2 g) was added dropwise to a solution of 3-(2-aminoethyl)-5-(n-nonyl)-2-(3-pyridyl)-thiazolidin-4-one (0.50 g, 1.43 mmol) in pyridine (2 ml) with stirring under cooling with ice. The mixture was left standing overnight at room temperature. To this solution was added saturated aqueous NaHCO$_3$ (30 ml), and the mixture was extracted with benzene. After drying of the extract, the solvent was removed therefrom by evaporation under reduced pressure, giving the intended 3-(2-acetylaminoethyl)-5-(n-nonyl)-2-(3-pyridyl)thiazolidin-4-one (0.52 g, 92% yield) as an oily form.

IR (CHCl$_3$) [cm$^{-1}$]; 3430, 2920, 2850, 1665, 1590, 1580, 1365

NMR (δ, CDCl₃, ppm); 1.95 (3H, s), 3.93 (0.45H, dd, 9.90 and 3.63Hz), 4.03 (0.55H, ddd, 9.24, 3.63 and 1.65Hz), 5.75 (0.55H, d, 1.65Hz), 5.76 (0.45H, s), 6.06-6.11 (1H, m)

EXAMPLE 13

Preparation of 3-(2-dimethylaminoethyl)-5-(n-nonyl)-2-(3-pyridyl)-thiazolidin-4-one (trans-isomer)

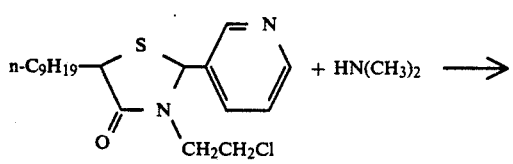

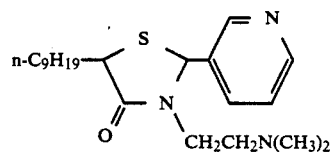

A 50% aqueous dimethylamine solution (1.0 ml, 11 mmol) was added to a solution of trans-isomer (128 mg, 0.35 mmol) of 3-(2-chloroethyl)-5-(n-nonyl)-2-(3-pyridyl)thiazolidin-4-one in dimethylsulfoxide (3 ml). The mixture, placed in a sealed tube, was heated at 100° C. for hours. After removal of the solvent by evaporation under reduced pressure, the residue was dissolved in chloroform (30 ml). The solution was washed twice with saturated aqueous NaHCO₃ and dried. Removal of the chloroform gave the intended trans-isomer (131 mg, quantitative yield) of 3-(2-dimethylaminoethyl)-5-(n-nonyl)-2-(3-pyridyl)thiazolidin-4-one as an oily form.

IR (CHCl₃) [cm⁻¹]; 2930, 2860, 1670, 1580, 1355,

NMR (δ, CDCl₃, ppm); 2.15 (6H, s), 2.24 (1H, dt, 12.87 and 5.61Hz), 2.46 (1H, ddd, 12.87, 7.20 and 5.94Hz), 2.69 (1H, ddd, 14.19, 7.20 and 5.61Hz), 3.80 (1H, ddd, 14.19, 5.94 and 5.61Hz), 4.03 (1H, ddd, 8.58, 3.96 and 1.98Hz), 5.86 (1H, d, 1.98Hz)

EXAMPLE 14

Isolation-separation of trans-isomer and cis-isomer 3-(2-Dimethylaminoethyl)-5-(n-nonyl)-2-(3-pyridyl)-thiazolidin-4-one (7.9 g) prepared in Example 2 was subjected to medium-pressure liquid chromatography (column size : 40 mm×500 mm, Silica gel-60 ®, carrier : hexane : ethanol : aqueous ammonium hydroxide =3000 : 300 : 50), giving the trans-isomer (1.42 g), the cis-isomer (3.42 g), and their mixture (2.77 g).

trans-isomer
IR (CHCl₃) [cm⁻¹], 2930, 2860, 1670, 1580, 1355,
NMR (δ, CDCl₃, ppm); 2.15 (6H, s), 4.0-4.06 (1H, m), 5.86 (1H, d, J=2.0Hz)
cis-isomer
IR (CHCl₃) [cm⁻¹]; 2930, 2860, 1670, 1590, 1360,
NMR (δ, CDCl₃, ppm); 2.13 (6H, s), 3.97 (1H, dd, J=3.7 and 9.8Hz), 5.84 (1H, s)

A 5% HCl in isopropanol (5 g, 7 mmol) was added to a portion (1 g, 2.65 mmol) of the obtained trans-isomer, and stirred for 1 hour at room temperature. The solvent was removed by evaporation under reduced pressure. The residue, subjected to recrystallization from a 1 : 3 ethanol-hexane mixture (5 ml), gave the hydrochloride of the trans-isomer (1.02 g, 85% yield).

m.p. 175.5°–178° C.
IR (KBr) [cm⁻¹]; 2920, 2850, 2660, 1670, 1460

EXAMPLE 15

Preparation of 3,5-dimethyl-2-(3-pyridyl)thiazolidin-4-one

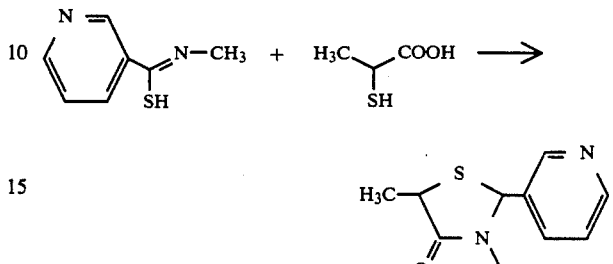

N-Nicotinylidenemethylamine (12.0 g, 0.1 mmol) was dissolved in toluene (100 ml) and thiolactic acid (10.6 g, 0.1 mol) was added. The mixture was subjected to azeotropic dehydration for 3 hours by Dean.Stack apparatus. The product mixture was cooled and washed with 5% aqueous NaHCO₃ solution, and dried. The solvent was removed in vacuo. The residue was subjected to recrystallization from ether, giving 3,5-dimethyl-2-(3-pyridyl)thiazolidin-4-one (15.6 g, 75% yield).

m.p. 89.5°–92° C.
IR (nujol) [cm⁻¹]; 1670, 1582, 1017, 719

EXAMPLE 16

3,5-Dimethyl-2-(3-pyridyl)thiazolidin-4-one (5 g) from Example 1 was subjected twice to recrystallization from a 1 : 1 ethyl acetate-hexane mixture, giving its cis-isomer. The filtrate was subjected to medium-pressure liquid chromatography (hexane-ethanol) to isolate the trans-isomer.
cis-isomer
m.p. 98.5°–99° C.
trans-Isomer
m.p. 81°–82°.C.

EXAMPLE 17

Preparation of 3,5-dimethyl-2-(3-pyridyl)thiazolidin-4-one

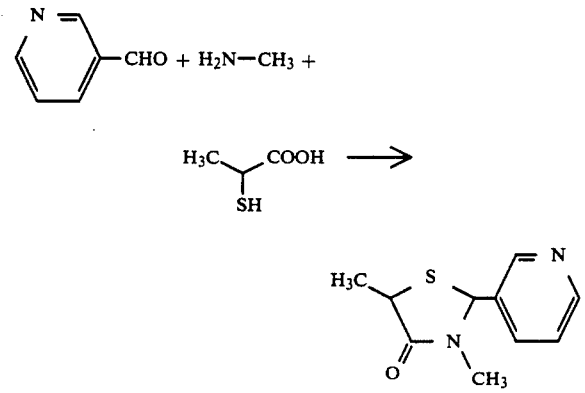

Nicotinaldehyde (10.7 g, 0.1 mol) was dissolved in toluene (100 ml), and a 40% aqueous methylamine (23.3 g, 0.3 mol) solution and thiolactic acid (10.6 g, 0.1 mol) were added. The mixture was subjected to azeotropic dehydration for 3 hours by Dean.Stack apparatus. The product mixture was cooled, washed with 5% aqueous NaHCO₃, and dried. The solvent was removed in vacuo, and the residue was subjected to recrystallization from ether, giving 3,5-dimethyl-2-(3-pyridyl)-thiazolidin-4-one (14.2 g, 68% yield).

m.p. 90°–92° C.

EXAMPLE 18

Preparation of 3-methyl-2-(3-pyridyl)thiazolidin-4-one

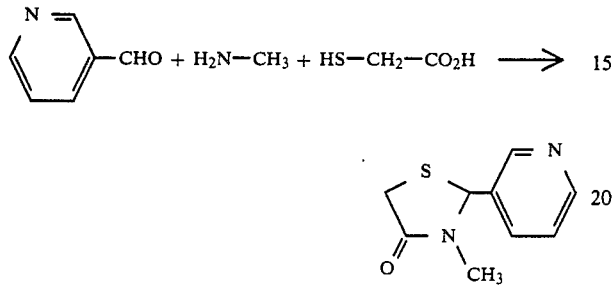

According to the procedure of Example 3, the title compound was prepared by using nicotinaldehyde, a 40% aqueous methylamine solution, and thioglycolic acid.

m.p. 96.5°–97.5° C.

IR (nujol) [cm⁻¹]; 1670, 1583, 1236, 1109, 1005, 717

EXAMPLE 19

Preparation of 5-methyl-2-(3-pyridyl)thiazolidin-4-one

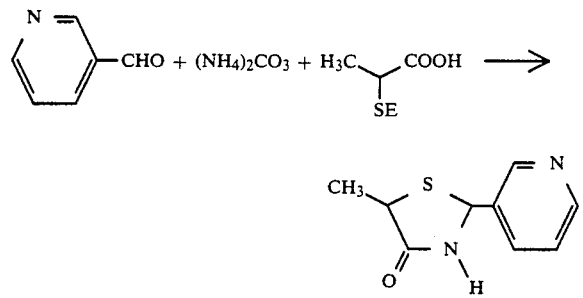

According to the procedure of Example 4, the title compound was prepared by using nicotinaldehyde, ammonium carbonate, and thiolactic acid.

m.p. 109.5°–110.5° C.

IR (nujol) [cm⁻¹]; 1680

EXAMPLE 20

Preparation of 3-(2-hydroxyethyl)-5-methyl-2-(3-pyridyl)thiazolidin-4-one

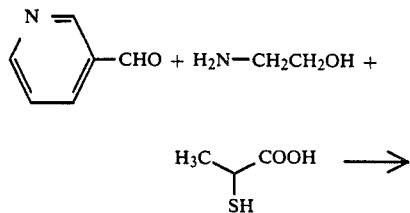

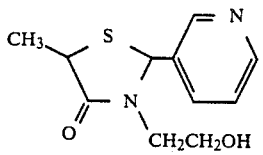

According to the procedure of Example 5, the title compound was prepared by using nicotinaldehyde, ethanolamine, and thiolactic acid.

NMR (δ, CDCl₃) [ppm]; 1.63 (1H, d, J=6.8Hz), 1.66 (2H, d, J=6.8Hz), 2.8–4.2 (6H, m), 5.83 (1H, s)

IR (CHCl₃) [cm⁻¹]; 3400, 2940, 1670, 1593, 1580, 1450, 1360, 1070.

EXAMPLE 21

Preparation of 5-butyl-3-methyl-2-(3-pyridyl)thiazolidin-4-one

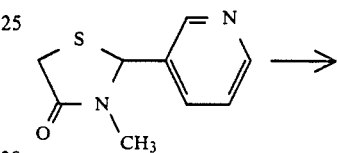

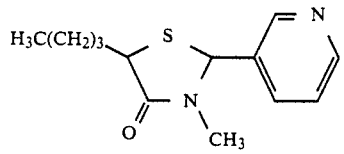

Dry diisopropylamine (1 ml, 5.7 mmol) was added to dry tetrahydrofuran (3 ml), and a butyllithium solution (3.9 ml, 6.2 mmol) in hexane was added dropwise at −40° C., the miXture was kept at −10° C. for 1 hour. A solution of 3-methyl-2-(3-pyridyl)thiazolidin-4-one (1 g, 5.2 mmol) in dry tetrahydrofuran (7 ml) was added dropwise to the mixture at −20° to −10° C. After this reaction mixture had been kept between those temperatures for 1 hour, there were added at −10° C. 1 bromobutane (0.78 g, 5.7 mmol) dissolved in tetrahydrofuran (2 ml), sodium iodide (0.77 g, 5.2 mmol), and hexamethylphosphorotriamide (1 ml). This reaction mixture was kept at room temperature for 2 hours. The resulting mixture, after addition of a phosphate buffer (pH 7.0), was extracted with ethyl acetate. The extract was dried over anhydrous Na₂SO₄ and filtered. The filtrate was concentrated by evaporation under reduced pressure. The residue was chromatographed on silica gel (hexane-ethyl acetate), giving 5-butyl-3-methyl-2-(3-pyridyl)thiazolidin-4-one (250 mg, 20% yield).

NMR (CDCl₃) δ[ppm]; 0.93 (3H, t, J=7.0Hz), 1.2–2.3 (6H, m), 2.74 (3H, m), 3.9–4.3 (1H, m), 5.4–5.5 (1H, m)

IR (CHCl₃) [cm⁻¹]; 2925, 2855, 1670, 1590, 1578, 1390, 1303, 1020

EXAMPLE 22

Preparation of 5,5,3-trimethyl-2-(3-pyridyl)thiazolidin-4-one

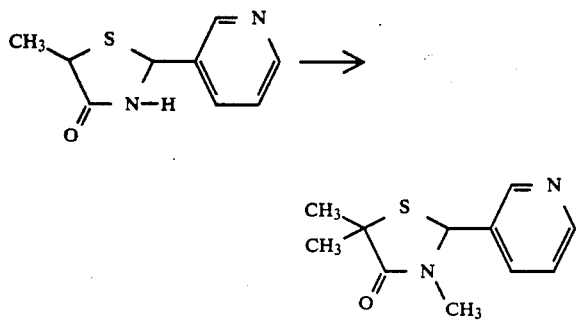

Dry diisopropylamine (0.95 ml, 5.3 mmol) was added to dry tetrahydrofuran (3 ml). Further a butyllithium solution (3.6 ml, 5.8 mmol) in hexane was added dropwise at −40° C. The mixture was kept at −10° C. for 1 hour. Then a solution of 3,5-dimethyl-2-(3-pyridyl)-thiazolidin-4-one (1 g, 4.8 mmol) in dry tetrahydrofuran (7 ml) was added dropwise at −20° to −10° C. After this reaction mixture had been kept between those temperatures for 1 hour, methyl iodide (0.75 g, 5.3 mmol) in dry tetrahydrofuran (2 ml) was added at −20° to −10° C. This reaction mixture was warmed up to 0° C. during 2 hours and then kept at the same temperature for 2 hours. The resulting mixture, after addition of a phosphate buffer (pH 7.0), was extracted with ethyl acetate. The extract was dried over anhydrous $Na_2SO_4$ and filtered. The filtrate was concentrated under reduced pressure, and subjected to medium-pressure liquid chromatography (hexane-acetone) and then to recrystallization from a 1 : 1 ether-hexane mixture, giving 5,5,3-trimethyl-2-(3-pyridyl)thiazolidin-4-one (0.42 g, 39% yield).

NMR (CDCl$_3$) δ[ppm]; 1.62 (3H, s), 1.68 (3H, s), 2.74 (3H, s), 5.51 (1H, s)

IR (nujol) [cm$^{-1}$]; 1668, 1590, 1390, 1310, 1135, 1071, 1021

EXAMPLE 23

Preparation of 5,5-di(cyclohexylmethyl)-3-methyl-2-(3-pyridyl)thiazolidin-4-one

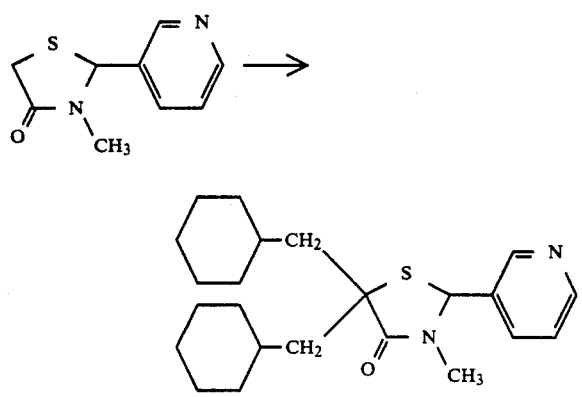

Dry diisopropylamine (2.76 ml, 15.8 mmol) was added to dry tetrahydrofuran (9 ml). Further, a n-butyllithium solution (10.6 ml, 16.2 mmol) in hexane was added dropwise at −20° to −30° C. The mixture was kept between those temperatures for 1 hour. Then a solution of 3-methyl-2-(3-pyridyl)thizodilin-4-one (3 g, 15.4 mmol) in dry tetrahydrofuran was added dropwise at −78° C. After this reactio mixture had been kept at the same temperature for 1 hour, bromomethylcyclohexane (3.01 g, 17.0 mmol) and sodium iodide (2.31 g, 15.4 mmol) were added at −78° C. This reaction mixture was warmed up to room temperature and kept standing overnight. The resulting mixture, after addition of aqueous NaCl, was extracted with ethyl acetate. The extract was washed with aqueous NaCl, dried, and the solvent was removed in vacuo. The residue was chromatographed on silica gel, giving 5,5-di(cyclohexylmethyl)-3-methyl-2-(3-pyridyl)thiazolidin-4-one (250 mg, 4.2 mg, 4.2% yield).

IR (CHCl$_3$) [cm$^{-1}$]; 2920, 1675, 1640, 1390

EXAMPLE 24

Preparation of 3-ethoxycarbonylmethyl-5-methyl-2-(3-pyridyl)-thiazolidin-4-one

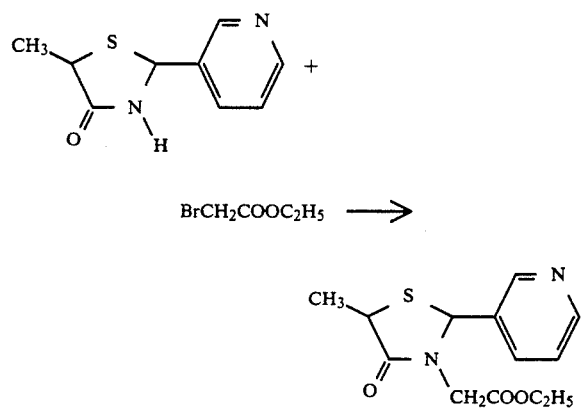

5-Methyl-2-(3-pyridyl)thiazolidin-4-one (10 g, 51.5 mmol) (cis and trans mixture) and ethyl bromoacetate (6.85 ml, 61.8 mmol) were dissolved in dry dimethylformamide (50 ml), and 60% sodium hydride (2.16 g, 54.1 mmol) was added portionwise to the solution at 0° to 10° C. This reaction mixture was kept between those temperatures for 1 hour. The mixture, after addition of aqueous NaCl, was extracted with ethyl acetate. The extract was washed with aqueous NaCl, dried, and the solvent was removed in vacuo. The residue was chromatographed on silica gel, giving the cis-isomer (5.8 g) and the trans-isomer (2.1 g) of the title compound (55% yield).

cis-isomer

NMR (CDCl$_3$, δ) [ppm]; 1.24 (3H, t, J=7.2Hz), 1.67 (3H, d, J=7.1 Hz), 5.81 (1H, s)

IR (CHCl$_3$) [cm$^{-1}$; 2950, 1740, 1683, 1587, 1575, 1441, 1370, 1014 trans-isomer

NMR (CDCl$_3$, δ) [ppm]; 1.25 (3H, t, J=7.2Hz), 1.68 (3H, d, J=7.1 Hz), 5.83 (1H, d, J=1.7Hz)

IR (CHCl$_3$) [cm$^{-1}$]; 2950, 1739, 1685, 1585, 1572, 1370, 1345, 1012

EXAMPLE 25

Preparation of 3-(2-chloroethyl)-5-methyl-2-(3-pyridyl)thiazolidin-4-one

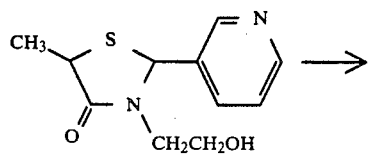

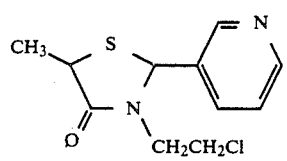

3-(2-Hydroxyethyl)-5-methyl-2-(3-pyridyl)thiazolidin-4-one (18.75 g, 78.7 mmol) was dissolved in methylene chloride (200 ml). Pyridine (9.55 ml, 118 mmol) was added and further, thionyl chloride (20 ml, 274 mmol) was added dropwise over 2 hours at 0° to 5° C. This reaction mixture was kept between those temperatures for 5 hours. The resulting mixture was washed with aqueous NaHCl$_3$ and aqueous NaCl, dried, and the solvent was removed in vacuo. The residue was chromatographed on silica gel and upon recrystallization from hexane-ether, to give 2,5-cis-3-(2-chloroethyl)-5-methyl-2-(3-pyridyl)thiazolidin-4-one (7.11 g) and 2,5-trans-3-(2chloroethyl)-5-methyl-2-(3pyridyl)thiazolidin-4-one (3.11 g), (51% yield).

cis-isomer, m.p. 76°–77° C.
trans-isomer, m.p. 112.5°–113.5° C.

EXAMPLE 26

Preparation of 3-(2-methoxyethyl)-5-methyl-2-(3-pyridyl)thiazolidin-4-one

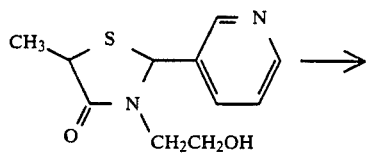

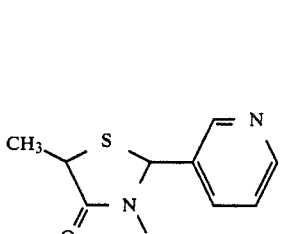

Methyl iodide (0.72 g, 5.0 mmol) was added to a solution of 3-(2-hydroxyethyl)-5-methyl-2-(3-pyridyl)-thiazolidin-4-one (1 g, 4.2 mmol) in dry dimethylformamide (5 ml), and 40% sodium hydride (176 mg, 4.4 mmol) was added portionwise to the mixture under ice-cooling. Then, the mixture was kept cooling for 1 hour. The resulting mixture was poured into aqueous NaCl, and extracted with ethyl acetate. The extract was washed with water, dried over anhydrous Na$_2$SO$_4$, and filtered. The filtrate was concentrated and subjected to medium-pressure chromatography (hexane-acetone), giving 3-(2-methoxyethyl)-5-methyl-2-(3-pyridyl)-thiazolidin-4-one (0.51 g, 48% yield).

NMR (CDCl$_3$) δ[ppm]; 1.62 (0.75H, d, J=7.1 Hz), 1.66 (2.5H, d, J=7.1 Hz), 3.28 (2.25H, s), 3.3 (0.75H, s), 5.85 (1H, s).

IR (CHCl$_3$) [cm$^{-1}$]; 2935, 1670, 1589, 1576, 1445, 1408, 1300, 1113

EXAMPLE 27

Preparation of 3-(2-acetoxyethyl)-5-methyl-2-(3-pyridyl)thiazolidin-4-one

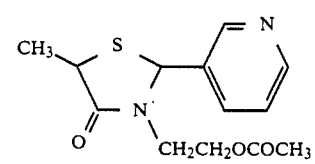

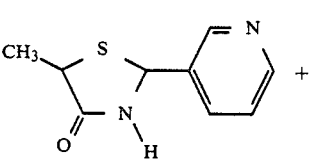

Pyridine (0.5 ml) was added to a solution of 3-(2-hydroxyethyl)-5-methyl-2-(3-pyridyl)thiazolidin-4-one (0.5 g, 2.1 mmol) in acetic anhydride (2 ml) under ice-cooling. Then, the mixture was kept cooling for 2 hours. The resulting mixture was concentrated by evaporation under reduced pressure, and subjected to medium-pressure chromatography (hexane-acetone), giving 3-(2-acetoxy-ethyl)-5-methyl-2-(3-pyridyl)thiazolidin-4-one (0.45 g, 77% yield)

NMR (CDCl$_3$) δ[ppm]; 1.62 (1H, d, J=7.1 Hz), 1.66 (2H, d, J=7.1 Hz), 2.06 (3H, s), 5.74 (1H, s).

IR (CHCl$_3$) [cm ]; 2960, 1740, 1693, 1590, 1579, 1350, 1020

EXAMPLE 28

Preparation of 3-t-butyloxycarbonylmethyl-5-methyl-2-(3-pyridyl)-thiazolidin-4-one

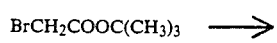

BrCH$_2$COOC(CH$_3$)$_3$ ⟶

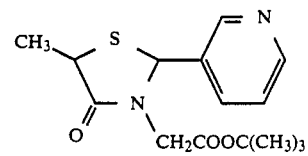

According to the procedure of Example 24 the trans-isomer and the cis-isomer of the title compound were prepared by using 5-methyl-2-(3-pyridyl)thiazolidin-4-one, t-butyl bromoacetate, and sodium hydride.

trans-isomer, m.p. 132°–133° C.
IR (nujol) [cm$^{-1}$]; 1738, 1690, 1679, 1572, 1260, 1164 cis-isomer, m.p. 108°–108.5° C.

IR (nujol) [cm⁻]; 1738, 1681, 1694, 1591, 1575, 1247, 1170

EXAMPLE 29

Preparation of 3-(2-acetylthioethyl)-5-methyl-2-(3-pyridyl)thiazolidin-4-one

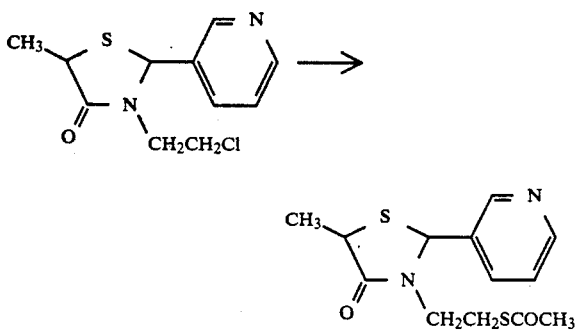

Potassium thioacetate (0.53 g, 4.7 mmol) was added to a solution of 2,5-trans-3-(2-chloroethyl)-5-methyl-2-(3pyridyl)thiazolidin-4-one (1 g, 3.9 mmol) in dimethylformamide (5 ml) and the mixture was stirred for 1 hour under ice-cooling. The resulting mixture, after addition of aqueous NaHCO₃, was extracted with ethyl acetate. The extract was washed with aqueous NaCl, dried, and the solvent was removed in vacuo. The residue was chromatographed on silica gel, giving 2,5-trans-3-(2-acetylthioethyl)-5-methyl-2-(3-pyridyl) thiazolidin-4-one (0.85 g, 78% yield).

The cis-isomer also was prepared as stated above.
trans-isomer, m.p. 60°–62° C.
cis-isomer, m.p. 55°–56.5° C.

EXAMPLE 30

Preparation of 5-(4-chlorophenyl)-3-methyl-2-(3-pyridyl)-1-oxo-thiazolidin-4-one

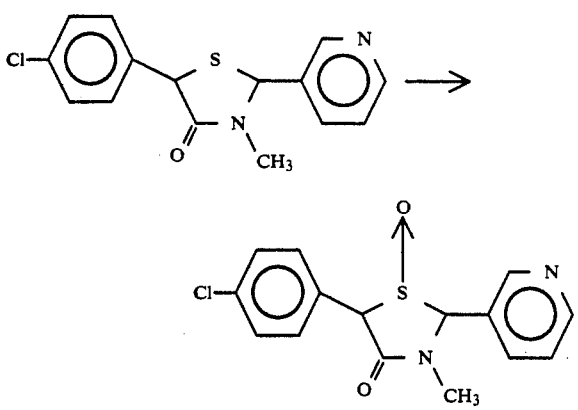

The isomer I (3 g, 0.0098 mol) obtained in Example 2 was dissolved in dichloromethane (30 ml) and therein was charged in parts m-chloroperbenzoic acid (2.04 g, 0.0118 mol) under ice-cooling. After the reaction was finished, aqueous NaHCO₃ and aqueous Na₂SO₃ were added and the reaction mixture was extracted with dichloromethane. The extract was dried and concentrated under reduced pressure and the residue was purified by silica gel chromatography (10% acetone-chloroform) and recrystallized from ether to obtain 5-(4-chlorophenyl)-3-methyl-2-(3-pyridyl)-1-oxo-thiazolidin-4-one (1.85 g).

m.p. 149°–153° C.

IR (nujol) cm⁻¹; 1705, 1688, 1577, 1260, 1088, 1062.

EXAMPLE 31

Preparation of 5-(4-chlorophenyl)-3-methyl-2-(3-pyridyl)-1-oxo-thiazolidin-4-one

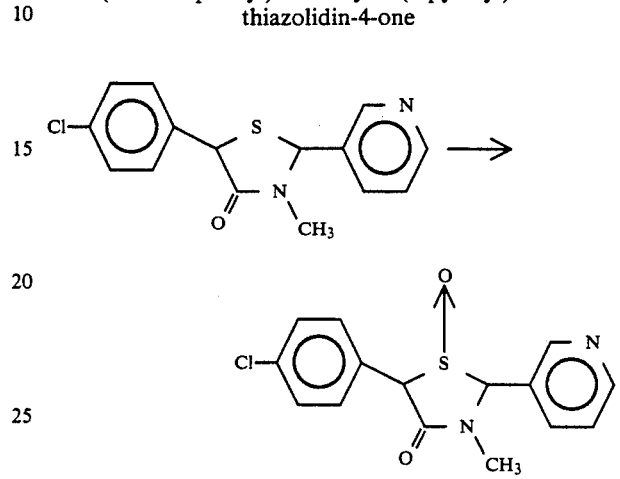

The isomer II (3.95 g, 0.013 mol) obtained in Example 2 was dissolved in dichloromethane (40 ml) and therein was charged in parts m-chloroperbenzoic acid (3.35 g, 0.019 mol) under ice-cooling. After the reaction was finished, thereto were added aqueous NaHCO₃ and aqueous Na₂SO₃ and the reaction mixture was extracted with dichloromethane. The extract was dried and concentrated under reduced pressure and the residue was purified by silica gel chromatography (10% acetone-chloroform) and recrystallized from ether to obtain 5-(4-chlorophenyl)-3-methyl-2-(3-pyridyl)-1-oxy-thiazolidin-4-one (1.8 g, yield) 43%).

m.p. 144°–145° C.

IR (nujol) cm⁻¹; 1686, 1575, 1259, 1085, 1062.

EXAMPLE 32

Preparation of 5-(4-chlorophenyl)-3-methyl-2-(3-pyridyl)-1,1-dioxo-thiazolidin-4-one.hydrochloride

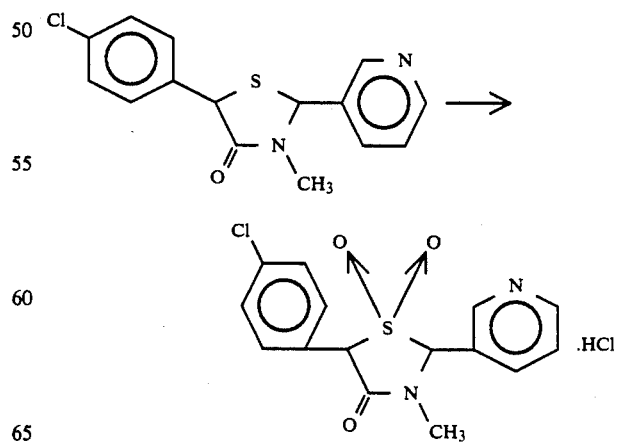

5-(4-Chlorophenyl)-3-methyl-2-(3-pyridyl)triazolidin-4-one (0.15 g, 0.00049 mol) obtained in Example 1 was dissolved in chloroform (30 ml) and therein was charged in parts m-chloroperbenzoic acid (0.52 g, 0.003 mol) under ice-cooling. The mixture was stirred for 1 hour under ice-cooling and then warmed to room temperature. After 10 hours, the solvent was distilled off under reduced pressure and the residue was treated with ether. The ether layer was removed and the residue was dried under reduced pressure and dissolved in isopropyl alcohol (3 ml) containing 10% hydrochloric acid. The solution was added dropwise to ether under ice-cooling to obtain 5-(4-chlorophenyl)-3-methyl-2-(3-pyridyl)-1,1-dioxo-thiazolidin-4-one hydrochloride (0.90 g). m.p. 120°–123° C.

REFERENCE EXAMPLE 8

Optical resolution of α-phenyl-α-mercaptoacetic acid derivative.

(+)-α- ercapto-α-(4-chlorophenyl)acetic acid cinchonidine (43.9 g, 0.150 mol) was suspended in deaerated ethanol (900 ml) and thereto was added a solution of (±)-α-mercapto-α-(4-chlorophenyl)acetic acid (30.2 g, 0.150 mol) in deaerated ethanol (50 ml) at 30° C. with stirring. Then, stirring was discontinued and the mixture was left to stand for 2 hours at room temperature. The precipitated crystal was collected by filtration and dried to obtain a crude salt-(1) (42.6 g, 58%).

The resulting crude salt-(1) (42.6 g) was dissolved in deaerated ethanol (2000 ml) at 80° C. with stirring. Then, stirring was discontinued and the solution was left at room temperature for 48 hours. The precipitated crystal was collected by filtration and dried to obtain a crude salt-(2) (22.9 g, 31% yield). This crude salt-(2) (22.5 g) was dissolved in deaerated ethanol (1000 ml) at 80° C. with stirring. Then, stirring was discontinued and the solution was left at room temperature for 20 hours. The precipitated crystal was collected by filtration and dried to obtain purified cinchonidine salt of (+)-α-mercapto-α-(4-chlorophenyl)acetic acid (15.8 g, 21% yield).

Then, to this purified salt were added 10% aqueous $H_2SO_4$ (100 ml) and methanol (20 ml) to effect decomposition and the product was extracted twice with ether. The organic layer was dried and the solvent was distilled off under reduced pressure to obtain (+)-α-mercapto-α-(4-chlorophenyl)acetic acid (5.93 g, 20% yield).

m.p. 123°–125° C.

$[\alpha]_D^{17} = +84.8°$ (c 0.748, EtOH)

REFERENCE EXAMPLE 9

(−)- α-Mercapto-α-(4-chlorophenyl)acetic acid

Cinchonine (54.7 g, 0.186 mol) was suspended in deaerated ethanol (270 ml) and thereto was added a solution of (±)-α-mercapto-α-(p-chlorophenyl)acetic acid (37.6 g, 0.186 mol) in deaerated ethanol (190 ml) at room temperature with stirring. Then, stirring was discontinued and the mixture was left to stand for 10 hours at room temperature. The precipitated crystal was collected by filtration and dried to obtain a crude salt-(1) (33.0 g, 36%).

The resulting crude salt-(1) (32.8 g) was dissolved in deaerated ethanol (550 ml) at 80° C. with stirring. Then, stirring was discontinued and the solution was left at room temperature for 24 hours. Gentle stirring was further effected for 2 hours and the precipitated crystal was collected by filtration and dried to obtain purified cinchonine salt of (−)-α-mercapto-α-(4-chlorophenyl)acetic acid (10.8 g, 12% yield).

Then, to this purified salt were added 10% aqueous $H_2SO_4$ (50 ml) and methanol (10 ml) to effect decomposition and the product was extracted twice with ether. The organic layer was dried and the solvent was distilled off under reduced pressure to obtain (−)-α-mercapto-α-(4-chlorophenyl)acetic acid (4.45 g, 12% yield).

m p. 123°–125° C.

$[\alpha]_D = -84.1°$ (c 0 503, EtOH)

EXAMPLE 33

Preparation of (+)-cis-5-(4-chlorophenyl)-3-methyl-2-(3-pyridyl)-thiazolidin-4-one A solution of N-nicotinylidenemethylamine (6.37 g, 0.053 mol) in tetrahydrofuran (20 ml) was added dropwise to a solution of (+)-α-mercapto-α-(4-chlorophenyl)acetic acid (10.72 g, 0.053 mol) in tetrahydrofuran (100 ml) with stirring under ice-cooling. The reaction was allowed to proceed for 10 hours. To the reaction mixture was added toluene (50 ml) and the solvent was distilled off under reduced pressure. The resulting crude product was cooled to 0°–5° C. and crystallized to give a crude crystal (17.15 g). This crude crystal was recrystallized from ether at 0°–5° C. to obtain (+)-cis-5(4-chlorophenyl)-3-methyl-2-(3-pyridyl)thiazolidin-4-one (9.36 g, 58% yield).

m.p. 77.5°–79.0° C.

$[\alpha]_D^{27} = +26.7°$ (c 0.60, $CHCl_3$)

EXAMPLE 34

Preparation of (−)-cis-5-(4-chlorophenyl)-3-methyl-2-(3-pyridyl)-thiazolidin-4-one Examples 1 and 2 were repeated using (−)-α-mercapto-α-(4-chlorophenyl)acetic acid (6.11 g, 0.030 mol) and N-nicotinylidenemethylamine (3.63 g, 0.030 mol) to obtain (−)-cis-5-(4-chlorophenyl)-3-methyl-2-(3-pyridyl)thiazolidin-4-one (5.52 g, 60% yield).

m.p. 75.0°–77.5° C.

$[\alpha]_D^{26} = -25.5°$ (c 0.60, $CHCl_3$)

EXAMPLE 35

Preparation of (−)-trans-5-(4-chlorophenyl)-3-methyl-2-(3-pyridyl) thiazolidin-4-one and its (+)-cis isomer Molecular Sieves 4A (1.0 g) was added to a solution of (+)-α-mercapto-α-(4-chlorophenyl)acetic acid (0.83 g, 4.1 mmol) and N-nicotinylidenemethylamine (0.49 g, 4.1 mmol) in toluene (10 ml) and reaction was allowed to proceed for 3 hours with stirring at 50° C. Then, Molecular Sieves were removed by filtration and the solvent was distilled off under reduced pressure from the filtrate to obtain a crude product. This crude product was purified by silica gel chromatography (hexane : dichloromethane : ethanol =5 : 1 : 1) obtain an earlier eluted compound (−)-trans-5-(4-chlorophenyl)-3-methyl-2-(3-pyridyl)thiazolidin-4-one (0.19 g, 15% yield) and a later eluted compound (+)-cis-5-(4-chlorophenyl)-3-methyl-2-(3-pyridyl)-thiazodidin-4-one (0.60 g, 48% yield).

(−)-Trans isomer:

m.p. 137°–138° C.

$[\alpha]_D^{28} = -54.8°$ (c 1.17, $CHCl_3$)

(+)-Cis isomer:
m.p. 77°-79° C.
$[\alpha]_D^{28} = +26.6°$ (c 0.70, CHCl$_3$)

EXAMPLE 36

Preparation of
(+)-trans-5-(4-chlorophenyl)-3-methyl-2-(3-pyridyl)-thiazolidin-4-one Procedure of Examples 1 and 2 were repeated using (−)-α-mercapto-α-(4-chlorophenyl)acetic acid (0.65 g, 3.2 mmol) and N-nicotinylidenemethylamine (0.38 g, 3.2 (3-pyridyl)thiazolidin-4-one (0.16 g, 16% yield).
m.p. 135°-137° C.
$[\alpha]_D^{27} = +52.7°$ (c 1.02, CHCl$_3$)

EXAMPLE 37

Preparation of
(+)-cis-3,5-dimethyl-2-(3-pyridyl)thiazolidin-4-one

A solution of N-nicotinylidenemethylamine (4.37 g, 36 mmol) in tetrahydrofuran (20 ml) was added dropwise to a solution of (−)-2-mercaptopropionic acid (3.86 g, 36 mmol) in tetrahydrofuran (40 ml) with stirring under a stream of nitrogen while cooling with ice. The reaction was allowed to proceed for 12 hours.

Then, the product mixture was dissolved in ethyl acetate (50 ml) and the solution was washed in turn with saturated aqueous NaHCO$_3$ (20 ml), water (20 ml), and aqueous NaCl, and dried. The solvent was removed under reduced pressure, giving a crude product (6.97 g), which was then washed with ether (10 ml) at 0° to 5° C. and, upon recrystallization from ether (10 ml), gave (+)-cis-3,5-dimethyl-2-(3-pyridyl)thiazolidin-4-one (3.77 g, 50% yield).
m.p. 66.5°-68.5° C.
$[\alpha]_D^{26} = +20.5°$ (C 0.44, CHCl$_3$)

EXAMPLE 38

Preparation of
(-)-cis-3,5-dimethyl-2-(3-pyridyl)thiazolidin-4-one

According to the procedure of Example 29, the title compound (3.24 g, 52% yield) was prepared from (+)-2-mercaptopropionic acid (3.19 g, 30 mmol) and N-nicotinylidenemethylamine (3.61 g, 30 mmol).
m.p. 66.0°-68.5° C.
$[\alpha]_D^{25} = -21.3°$ (C 3.28, CHCl$_3$)

EXAMPLE 39

Preparation of
(−)-trans-3,5-dimethyl-2-(3-pyridyl)thiazolidin-4-one

Titanium tetraisopropoxide (1.42 g, 5.0 mmol) was added to a solution of (−)-2-mercaptopropionic acid (0.53 g, 5.0 mmol) in dichloromethane (5 ml) with stirring at room temperature under a stream of nitrogen. Then, a solution of N-nicotinylidenemethylamine (0.60 g, 5.0 mmol) in dichloromethane (2 ml) was similarly added dropwise at room temperature. The reaction was allowed to proceed for 5 hours. The product mixture, after addition of water, was celite-filtered using dichloromethane (20 ml) as washing solvent. The resulting organic layer was washed with water (10 ml) and then with aqueous NaCl, and dried. The solvent was removed under reduced pressure, leaving a crude product (0.44 g). Purification thereof by silica gel flash chromatography (hexane : 2-propanol =4 : 1) gave (−)-trans-3,5-dimethyl-2-(3-pyridyl)thiazolidin-4-one (54 mg) in oily form.
$n_D^{26} = 1.6043$
$[\alpha]_D^{25} = -132.5°$ (C 0.28, CHCl$_3$)

EXAMPLE 40

Preparation of
(+)-trans-3,5-dimethyl-2-(3-pyridyl)thiazolidin-4-one

According to the procedure of Example 39, the title compound (49 mg) in oily form was prepared from (+)-2-mercaptopropionic acid (0.53 g, 5.0 mmol), titanium tetraisopropoxide (1.42 g, 5.0 mmol), and N-nicotinylidenemethylamine (0.60 g, 5.0 mmol)
$n_D^{26} = 1.6039$
$[\alpha]_D^{24} = +130.8°$ (C 0.34, CHCl$_3$)

EXAMPLE 41

Preparation of
3-(2-(5-(4-chlorophenyl)-3-methyl-4-oxo)thiazolidinyl-1-methylpyridinium iodide

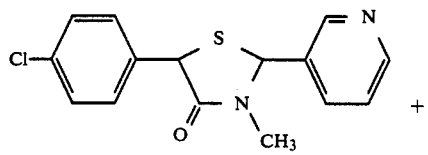

CH$_3$I ⟶

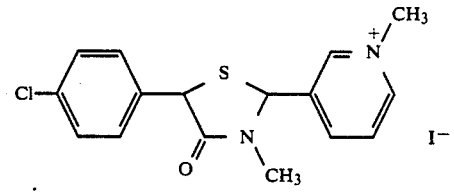

The isomer I (2.0 g 0.0066 mol) obtained in Example 2 was dissolved in acetone (33 ml) and therein was charged methyl iodide (4.7 g). After stirring at room temperature for 8 hours, crystals formed were colected by filtration. After washing with acetone, the crystals were dried under reduced pressure to obtain the objective compound (isomer I'). The reaction was quantitative.

By carrying out a reaction similar to the above, from the isomer II obtained in Example 2, the objective compound (isomer II') was obtained.
m.p. of isomer I': 175°-177° C.
m.p. of isomer II': 179.5°-182.5° C.

The compounds as shown in the following table were prepared in accordance with the processes of Examples 1-41 and Reference Examples 1-9.

| Example | n | R$^1$— | R$^2$— | R$^3$— | P— |
|---|---|---|---|---|---|
| 42 | 0 | F—⟨O⟩— | H— | CH$_3$— | ⟨O⟩—N |

-continued
| Example | n | R¹— | R²— | R³— | P— |
|---|---|---|---|---|---|
| 43 | 0 | 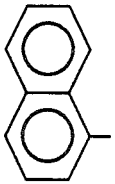 | " | " | " |
| 44 | 0 | " | " | " | 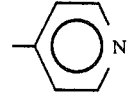 |
| 45 | 0 | " | " | " | 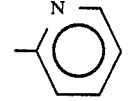 |
| 46 | 0 | 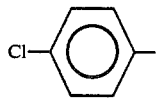 | " | " | 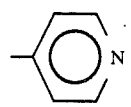 |
| 47 | 0 | " | " | " | 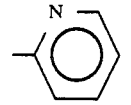 |
| 48 | 0 | 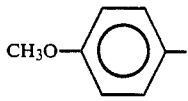 | " | " | 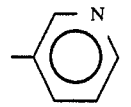 |
| 49 | 0 | 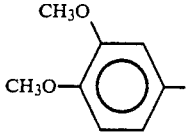 | H— | $CH_3$— | 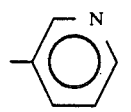 |
| 50 | 0 | 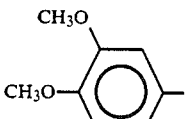 | " | " | " |
| 51 | 0 | 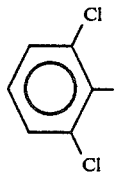 | " | " | " |
| 52 | 0 | 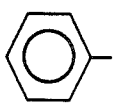 | " | " | " |
| 53 | 0 | 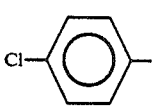 | " | $CH_3CH_2$— | " |
| 54 | 0 | " | , Rf high | " | $CH_2=CHCH_2$— | " |

| Example | n | R¹— | R²— | R³— | P— |
|---|---|---|---|---|---|
| 55 | 0 | " | , Rf low | " | " |
| 56 | 0 | " | , Rf high | CH≡CCH₂— | " |
| 57 | 0 | 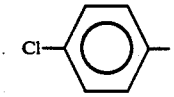 Cl—⌬— | H—, Rf low | CH≡CCH₂— | 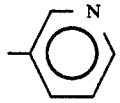 ⌬N |
| 58 | 0 | " | , Rf high | 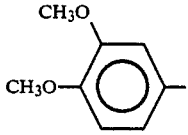 CH₃O—⌬—, CH₃O— | " |
| 59 | 0 | " | , Rf low | " | " |
| 60 | 0 | " | , Rf high | H— 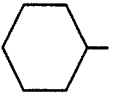 ⌬— | " |
| 61 | 0 | " | Rf low | " | " |
| 62 | 0 | " | Rf high |  ⌬—CH₂CH₂— (cyclohexyl-ethyl) | " |
| 63 | 0 | " | , Rf low | " | " |
| 64 | 0 | " | " | HOCH₂CH₂— | " |
| 65 | 0 | " | " | HOCH₂CH₂CH₂— | " |
| 66 | 0 | 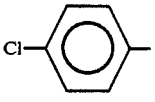 Cl—⌬— | H— | HO\|CHCH₂—\|CH₃ | 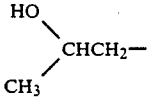 ⌬N |
| 67 | 0 | " | , Rf high | 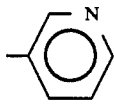 ⌬—CH₂CH₂— | " |
| 68 | 0 | " | , Rf low | " | " |
| 69 | 0 | " | , Rf high | O‖CH₃COCH₂CH₂— | " |
| 70 | 0 | " | , Rf low | " | " |
| 71 | 0 | " | , Rf high | O‖CH₃COCH₂CH₂CH₂— | " |
| 72 | 0 | " | , Rf high | O CH₃‖ \|CH₃COCHCH₂— | " |
| 73 | 0 | " | Rf low | " | " |
| 74 | 0 | 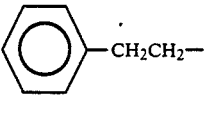 Cl—⌬— | H—, Rf high | CH₃\|NCH₂CH₂—\|CH₃ | 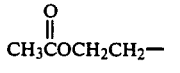 ⌬N |
| 75 | 0 | " | , Rf low | " | " |

-continued

| Example | n | R¹— | R²— | R³— | P— |
|---|---|---|---|---|---|
| 76 | 0 | Cl-phenyl (2-Cl), Rf high | " | $CH_3$— | " |
| 77 | 0 | " , Rf low | H— | $CH_3$— | " |
| 78 | 0 | OCH₃-phenyl (2-OCH₃), Rf high | " | " | " |
| 79 | 0 | " , Rf low | " | " | " |
| 80 | 0 | $CH_3$ | Trans | " | $CH_2CH_2CH_2N(CH_3)_2$ | " |
| 81 | 0 | | Cis | | | |
| 82 | 0 | n-$C_3H_7$ | Trans | H— | $CH_2CH_2N(CH_3)_2$ | 3-pyridyl |
| 83 | 0 | | Cis | | | |
| 84 | 0 | n-$C_4H_9$ | Trans | " | $CH_2CH_2N(CH_3)_2$ | " |
| 85 | 0 | | Cis | | | |
| 86 | 0 | n-$C_5H_{11}$ | Trans | " | $CH_2CH_2N(CH_3)_2$ | " |
| 87 | 0 | | Cis | | | |
| 88 | 0 | n-$C_6H_{13}$ | Trans | " | $CH_2CH_2N(CH_3)_2$ | " |
| 89 | 0 | | Cis | | | |
| 90 | 0 | n-$C_7H_{15}$ | Trans | " | $CH_2CH_2N(CH_3)_2$ | " |
| 91 | 0 | | Cis | | | |
| 92 | 0 | n-$C_8H_{17}$ | Trans | " | $CH_2CH_2N(CH_3)_2$ | " |
| 93 | 0 | | Cis | | | |
| 94 | 0 | n-$C_{10}H_{21}$ | Trans | H— | $CH_2CH_2N(CH_3)_2$ | 3-pyridyl |
| 95 | 0 | | Cis | | | |
| 96 | 0 | n-$C_{11}H_{23}$ | Trans | " | $CH_2CH_2N(CH_3)_2$ | " |
| 97 | 0 | | Cis | | | |
| 98 | 0 | n-$C_{12}H_{23}$ | Trans | " | $CH_2CH_2N(CH_3)_2$ | " |
| 99 | 0 | | Cis | | | |
| 100 | 0 | n-$C_{13}H_{27}$ | Trans | " | $CH_2CH_2N(CH_3)_2$ | " |
| 101 | 0 | | Cis | | | |
| 102 | 0 | n-$C_{14}H_{29}$ | Trans | H | $CH_2CH_2N(CH_3)_2$ | " |
| 103 | | | Cis | | | |
| 104 | 0 | n-$C_{15}H_{31}$ | Trans | H | $CH_2CH_2N(CH_3)_2$ | " |
| 105 | | | Cis | | | |
| 106 | 0 | n-$C_{16}H_{33}$ | Trans | H | $CH_2CH_2N(CH_3)_2$ | 3-pyridyl |
| 107 | | | Cis | | | |
| 108 | 0 | n-$C_{17}H_{35}$ | Trans | H | $CH_2CH_2N(CH_3)_2$ | " |
| 109 | | | Cis | | | |
| 110 | 0 | n-$C_{18}H_{37}$ | Trans | H | $CH_2CH_2N(CH_3)_2$ | " |
| 111 | | | Cis | | | |
| 112 | 0 | n-$C_{19}H_{39}$ | Trans | H | $CH_2CH_2N(CH_3)_2$ | " |
| 113 | | | Cis | | | |
| 114 | 0 | n-$C_{20}H_{41}$ | Trans | H | $CH_2CH_2N(CH_3)_2$ | " |
| 115 | | | Cis | | | |
| 116 | 0 | $CH_3$ | Trans | H | $CH_2CH_2N$(morpholino) | " |
| 117 | | | Cis | | | |
| 118 | 0 | n-$C_3H_7$ | Trans | H | $CH_2CH_2CH_2N(CH_3)_2$ | 3-pyridyl |
| 119 | | | Cis | | | |

-continued

| Example | n | R¹— | | R²— | R³— | P— |
|---|---|---|---|---|---|---|
| 120 | 0 | n-C₆H₁₃ | Trans | H | CH₂CH₂CH₂N(CH₃)₂ | " |
| 121 | | | Cis | | | |
| 122 | 0 | n-C₉H₁₉ | Trans | H | CH₂CH₂CH₂N(CH₃)₂ | " |
| 123 | | | Cis | | | |
| 124 | 0 | n-C₁₆H₃₃ | Trans | H | CH₂CH₂CH₂N(CH₃)₂ | " |
| 125 | | | Cis | | | |
| 126 | 0 | n-C₁₈H₃₇ | Trans | H | CH₂CH₂CH₂N(CH₃)₂ | " |
| 127 | | | Cis | | | |
| 128 | 0 | CH₃ | | CH₃ | CH₂CH₂CH₂N(CH₃)₂ | " |
| 129 | 0 | n-C₉H₁₉ | | H | CH₂(CH₂)CH₂N(CH₃)₂ | " |
| 130 | 0 | n-C₉H₁₉ | Trans | H | CH₂CH₂N(C₂H₅)₂ | 3-pyridyl |
| 131 | | | Cis | | | |
| 132 | 0 | n-C₉H₁₉ | Trans | H | CH₂CH₂NC₂H₅ | " |
| 133 | | | Cis | | H | |
| 134 | 0 | n-C₉H₁₉ | | H | CH₂CH₂N(pyrrolidinyl) | " |
| 135 | 0 | n-C₉H₁₉ | | H | CH₂CH₂N(piperazinyl-NH) | " |
| 136 | 0 | n-C₉H₁₉ | | H | CH₂CH₂NH₂ | " |
| 137 | 0 | n-C₉H₁₉ | | H | CH₂CH₂N(C₂H₅)(COCH₃) | " |
| 138 | 0 | (CH₃)₂CH(CH₂)₃CHCH₃(CH₃)₂ | Trans | H | CH₂CH₂N(CH₃)₂ | " |
| 139 | 0 | CH₂=CHCH₂ | Trans | H | CH₂CH₂N(CH₃)₂ | " |
| 140 | 0 | C₆H₅CH₂ | Trans | H | CH₂CH₂N(CH₃)₂ | 3-pyridyl |
| 141 | 0 | (CH₃)₂CH₂CH₂NH₂ | Trans | H | CH₂CH₂N(CH₃)₂ | " |
| 142 | 0 | H | | H | (CH₂)₂-C₆H₃(OCH₃)₂ | " |
| 143 | 0 | CH₃ | | " | CH₂CH₃ | " |
| 144 | 0 | " | Trans | " | CH₂CH=CH₂ | " |
| 145 | 0 | " | Cis | " | " | " |
| 146 | 0 | " | Trans | " | CH₂C≡CH | " |
| 147 | 0 | " | Cis | " | " | " |
| 148 | 0 | " | Trans | " | (CH₂)₂-C₆H₅ | " |
| 149 | 0 | " | Cis | " | " | " |
| 150 | 0 | CH₃ | Trans | H | (CH₂)₂-C₆H₃(OCH₃)₂ | 3-pyridyl |

-continued

| Example | n | R¹— | R²— | R³— | P— |
|---|---|---|---|---|---|
| 151 | 0 | " | " | 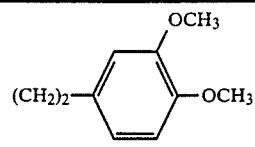 (CH₂)₂—C₆H₃(OCH₃)₂ | " |
| 152 | 0 | " | " | (CH₂)₃OCH₃ | " |
| 153 | 0 | " | Trans | " | CH₂CON(CH₃)₂ | " |
| 154 | 0 | " | Cis | " | " | " |
| 155 | 0 | CH₂CH₃ | | " | CH₃ | " |
| 156 | 0 | (CH₂)₂CH₃ | | " | " | " |
| 157 | 0 | CH₂CH(CH₃)₂ | | " | " | " |
| 158 | 0 | CH(CH₃)CH₂CH₃ | | " | " | " |
| 159 | 0 | (CH₂)₄CH₃ | | H | CH₃ | 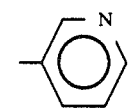 pyridyl |
| 160 | 0 | (CH₂)₅CH₃ | | " | " | " |
| 161 | 0 | (CH₂)₈CH₃ | | " | " | " |
| 162 | 0 | " | Trans | " | " | " |
| 163 | 0 | " | Cis | " | " | " |
| 164 | 0 | (CH₂)₉CH₃ | | " | " | " |
| 165 | 0 | (CH₂)₈CH₃ | Trans | " | 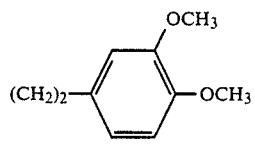 (CH₂)₂—C₆H₃(OCH₃)₂ | " |
| 166 | 0 | (CH₂)₈CH₃ | Cis | " | 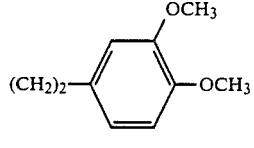 (CH₂)₂—C₆H₃(OCH₃)₂ | " |
| 167 | 0 | " | Trans | " | CH₂COOC₂H₅ | " |
| 168 | 0 | (CH₂)₈CH₃ | Cis | H | CH₂COOC₂H₅ | 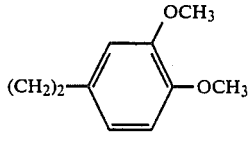 pyridyl |
| 169 | 0 | " | Trans | " | (CH₂)₂COOC₂H₅ | " |
| 170 | 0 | " | Cis | " | " | " |
| 171 | 0 | (CH₂)₁₅CH₃ | Trans | " | 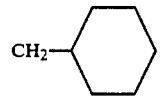 (CH₂)₂—C₆H₃(OCH₃)₂ | " |
| 172 | 0 | " | Cis | " | " | " |
| 173 | 0 | 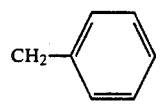 CH₂-cyclohexyl | | " | CH₃ | " |
| 174 | 0 | CH₂-phenyl | | " | " | " |
| 175 | 0 | (CH₂)₂CH₃ | | (CH₂)₂CH₃ | " | " |
| 176 | 0 | CH₂CH=CH₂ | | H | " | " |
| 177 | 0 | CH₂C≡CH | | H | " | " |

-continued

| Example | n | R¹— | R²— | R³— | P— |
|---|---|---|---|---|---|
| 178 | 0 | 4-Cl-C₆H₄— | H | H | 3-pyridyl |
| 179 | 1 | " | " | " | " |
| 180 | 1 | " | " | CH₃CH₂— | " |
| 181 | 0 | " | H | CH₃CH₂CH₂— | " |
| 182 | 1 | " | " | " | " |
| 183 | 0 | " | " | (CH₃)₂CHCH₂— | " |
| 184 | 1 | " | " | " | " |
| 185 | 0 | " | " | 4-Cl-C₆H₄-CH₂— | " |
| 186 | 1 | " | " | " | " |
| 187 | 1 | " | " | cyclohexyl— | " |
| 188 | 0 | 4-Cl-C₆H₄— | H | 2-furyl-CH₂— | 3-pyridyl |
| 189 | 1 | " | " | " | " |
| 190 | 1 | CH₃— | Cis | " | CH₃— | " |
| 191 | 0 | 4-Cl-C₆H₄— | " | (CH₃)₂CHOCH₂CH₂CH₂— | " |
| 192 | 1 | " | " | " | " |
| 193 | 0 | " | " | (CH₃CH₂O)₂CHCH₂— | " |
| 194 | 1 | 4-F-C₆H₄— | H | CH₃— | " |
| 195 | 0 | CH₃ | Trans | H | (CH₃)₂NCH₂CH₂— | " |
| 196 | 0 | CH₃ | Cis | H | " | " |
| 197 | 1 | 4-Cl-C₆H₄— | | H | HOCH₂CH₂CH₂— | 3-pyridyl |
| 198 | 0 | 2-F-C₆H₄— | " | CH₃— | " |
| 199 | 1 | " | " | " | " |

-continued

| Example | n | R¹— | R²— | R³— | P— |
|---|---|---|---|---|---|
| 200 | 0 | 3-fluorophenyl | " | " | " |
| 201 | 1 | " | " | " | " |
| 202 | 0 | n-C₇H₁₅— | " | " | " |
| 203 | 0 | n-C₈H₁₇— | " | " | " |
| 204 | 1 | " | " | " | " |
| 205 | 0 | 4-chlorophenyl | " | CH₃(CH₂)₃— | " |
| 206 | 1 | " | " | " | " |
| 207 | 0 | 4-chlorophenyl | H— | CH₃(CH₂)₄— | 3-pyridyl |
| 208 | 1 | " | " | " | " |
| 209 | 1 | 2-chlorophenyl | " | CH₃— | " |
| 210 | 1 | 2-methoxyphenyl | " | " | " |
| 211 | 0 | " | " | " | " |
| 212 | 0 | 2,6-difluorophenyl | Trans | " | " |
| 213 | 1 | " | " | " | " |
| 214 | 0 | " | Cis | " | " |
| 215 | 1 | 2,6-difluorophenyl | Cis | H— | CH₃ | 3-pyridyl |
| 216 | 0 | 2,4-difluorophenyl | Trans | " | " | " |
| 217 | 1 | " | " | " | " | " |
| 218 | 0 | " | Cis | " | " | " |
| 219 | 1 | " | " | " | " | " |

-continued

| Example | n | R¹— | R²— | R³— | P— |
|---|---|---|---|---|---|
| 220 | 0 | 4-F-C₆H₄— | Trans | " | " | " |
| 221 | 0 | " | Cis | " | " | " |
| 222 | 0 | 2-F-C₆H₄— | Trans | " | " | " |
| 223 | 0 | " | Cis | " | " | " |
| 224 | 1 | 4-F-C₆H₄— | Trans | H— | CH₃ | 3-pyridyl |
| 225 | 1 | " | Cis | " | " | " |
| 226 | 1 | 4-Cl-C₆H₄— | | " | 3,4-(CH₃O)₂-C₆H₃-CH₂CH₂— | " |
| 227 | 0 | 4-F-C₆H₄— | | " | CH₃CH₂— | " |
| 228 | 1 | " | | " | " | " |
| 229 | 0 | 4-F-C₆H₄— | | " | CH₃(CH₂)₃— | " |
| 230 | 1 | " | | " | " | " |
| 231 | 0 | " | | " | (CH₃)₂CHCH₂— | " |
| 232 | 1 | " | | " | " | " |
| 233 | 0 | 4-F-C₆H₄— | | H— | HOCH₂CH₂— | 3-pyridyl |
| 234 | 1 | " | | " | " | " |
| 235 | 0 | " | | " | CH₃CH₂CH₂— | " |
| 236 | 1 | " | | " | " | " |
| 237 | 0 | 2-F-C₆H₄— | | " | CH₃CH₂— | " |
| 238 | 1 | " | | " | " | " |
| 239 | 0 | " | | " | CH₃(CH₂)₃— | " |
| 240 | 1 | " | | " | " | " |

-continued

| Example | n | R¹— | R²— | R³— | P— |
|---|---|---|---|---|---|
| 241 | 0 | " | " | (CH₃)₂CHCH₂— | " |
| 242 | 1 | 2-F-C₆H₄— | H— | (CH₃)₂CHCH₂— | 3-pyridyl |
| 243 | 0 | 4-CF₃-C₆H₄— | " | CH₃— | " |
| 244 | 1 | " | " | " | " |
| 245 | 0 | " | Trans | " | " |
| 246 | 0 | " | Cis | " | " |
| 247 | 0 | 2-F-C₆H₄— | " | HOCH₂CH₂— | " |
| 248 | 1 | " | " | " | " |
| 249 | 0 | " | " | CH₃CH₂— | " |
| 250 | 1 | " | " | " | " |
| 251 | 0 | 2-F-C₆H₄— | H— | CH₂=CHCH₂— | 3-pyridyl |
| 252 | 1 | " | " | " | " |
| 253 | 0 | " | " | C₆H₅CH₂— | " |
| 254 | 1 | " | " | " | " |
| 255 | 0 | " | " | CH≡CCH₂— | " |
| 256 | 1 | " | " | " | " |
| 257 | 0 | 4-F-C₆H₄— | " | CH₂=CHCH₂— | " |
| 258 | 1 | " | " | " | " |
| 259 | 0 | " | " | C₆H₅CH₂— | " |
| 260 | 1 | " | " | " | " |
| 261 | 0 | 4-F-C₆H₄— | H— | CH≡CCH₂— | 3-pyridyl |
| 262 | 1 | " | " | " | " |
| 263 | 0 | " | " | CF₃CH₂— | " |

-continued

| Example | n | R¹— | R²— | R³— | P— |
|---|---|---|---|---|---|
| 264 | 0 | 4-Cl-C₆H₄— | " | C₂H₅OCCH₂—<br>‖<br>O | " |
| 265 | 1 | " | " | " | " |
| 266 | 0 | " | " | O<br>‖<br>H₂NCCH₂— | " |
| 267 | 1 | " | " | " | " |
| 268 | 0 | " | " | CH₃O—C₆H₃(OCH₃)—(CH₂)₂— | " |
| 269 | 0 | 4-Cl-C₆H₄— | H— | CH₃OCCH₂—<br>‖<br>O | pyridyl |
| 271 | 1 | " | " | " | " |
| 271 | 0 | " | " | C₆H₅—CH₂OCCH₂—<br>‖<br>O | " |
| 272 | 1 | " | " | " | " |
| 273 | 1 | " | " | (CH₃)₂NCH₂CH₂— | " |
| 274 | 0 | " | " | (CH₃)₂NCH₂CH₂CH₂— | " |

The values of Rf are those when development is effected with a diveloper, hexane : acetone=6 : 4 in TLC (silica gel). "Cis" and "Trans" show relation between the substituents at 2, 5 positions.

Physical properties of the above compounds are as follows:

| Example No. | Melting point of NMR (CDCl₃) δ ppm | (a) IR(CHCl₃) [cm⁻¹]<br>(b) IR(nujol) [cm⁻¹]<br>(c) IR(KBr) [cm⁻¹] |
|---|---|---|
| 42 | 2.79 (2H, s), 2.81 (1H, s), 5.08 (0.7H, s), 5.15 (0.3H, d, J = 1.9Hz), 5.60 (0.7H, s), 5.69 (0.3H, d, J = 1.9Hz) | CHCl₃: 1680, 1604, 1577, 1500, 1389, 1303, 1152, 1092 |
| 43 | 134~137° C. | nujol: 1692, 1584, 1020, 790 |
| 44 | 135.5~137.5° C. | nujol: 1665, 1597 |
| 45 | 96.5~98.5° C. | nujol: 1670, 1590, 793, 771 |
| 46 | 95.5~97° C. | nujol: 1675, 1595, 1086 |
| 47 | 147.5~148.5° C. | nujol: 1690, 1588, 1084, 1012 |
| 48 | 97~98° C. | nujol: 1681, 1668, (sh) 1513, 1036, 810 |
| 49 | 2.81 (3H, s), 3.88 (6H, s), 5.07 (0.75H, s), 5.14 (0.25H, d, J = 1.7Hz), 5.60 (0.75H, s), 5.68 (0.25H, d, J = 1.7Hz) | neat: 1680, 1513, 1260, 1139, 1025 |
| 50 | 119~120.5° C. | nujol: 1664, 1591, 1128, 1101 |
| 51 | 113.5~115° C. | nujol: 1690, 1578 |
| 52 | 184~150° C. | CHCl₃: 1683, 1595, 1581, 1390, 1309, 1100 |

-continued

| Example No. | Melting point of NMR (CDCl₃) δ ppm | (a) IR(CHCl₃) [cm⁻¹]<br>(b) IR(nujol) [cm⁻¹]<br>(c) IR(KBr) [cm⁻¹] |
|---|---|---|
| 53 | 1.01~1.1 (3H, m), 2.7~2.95 (1H, m), 3.65~3.9 (1H, m), 5.06 (0.5H, s), 5.12 (0.5H, d, J = 1.8Hz), 5.74 (0.5H, s), 5.81 (0.5H, d, J = 1.8 Hz) | CHCl₃: 2970, 1590, 1578, 1488, 1087, 1010 |
| 54 | 3.21 (1H, dd, J = 8.1, 15.1Hz), 4.4~4.5 (1H, m), 5.1, (1H, s), 4.9~5.3 (2H, m), 5.71 (1H, s), 5.6~5.8 (1H, m) | CHCl₃: 1690, 1590, 1578, 1496, 1401, 1306, 1089, 1011 |
| 55 | 3.16 (1H, dd, J = 7.9, 15.2Hz), 4.4~4.6 (1H, m), 5.16 (1H, d, J = 1.8Hz), 5.0~5.3 (2H, m), 5.55-5.75 (1H, m), 5.77 (1H, d, J = 1.8Hz) | CHCl₃: 2955, 1685, 1590, 1577, 1485, 1403, 1090, 1010 |
| 56 | 2.29 (1H, t, J = 2.6Hz), 3.54 (1H, dd, J = 2.6 & 7.5Hz), 4.69 (1H, dd, J = 2.6 & 7.5Hz), 5.10 (1H, s), 5.91 (1H, s) | CHCl₃: 3300, 1690, 1591, 1577, 1487, 1400, 1352, 1088 |
| 57 | 2.31 (1H, t, J = 2.6Hz), 3.33 (1H, dd, J = 2.6 & 7.5Hz), 4.70 (1H, dd, J = 2.6 & 7.5Hz), 5.15 (1H, d, J = 2.0Hz), 6.01 (1H, d, J = 2.0Hz) | CHCl₃: 3305, 1692, 1594, 1580, 1490, 1406, 1193 |
| 58 | 2.6~3.05 (3H, m), 3.84 (3H, s), 3.88 (3H, s), 3.8~4.0 (1H, m), 5.02 (1H, s), 5.31 (1H, s) | CHCl₃: 1675, 1589, 1573, 1484, 1460, 1145, 1085, 2930, 2835 |
| 59 | 2.6~3.0 (3H, m), 3.78 (3H, s), 3.90 (3H, s), 4.0~4.1 (1H, m), 5.06 (1H, d, J = 1.7 Hz), 5.42 (1H, d, J = 1.7Hz) | CHCl₃: 2940, 2845, 1680, 1593, 1579, 1490, 1360, 1094 |
| 60 | 0.8~1.9 (10H, m), 3.6~3.75 (1H, m), 5.03 (1H, s), 5.75 (1H, s) | CHCl₃: 2930, 2855, 1673, 1590, 1577, 1486, 1402, 1322, 1089, 1010 |
| 61 | 0.9~1.9 (10H, m), 3.75~3.9 (1H, m), 5.16 (1H, d, J = 1.7Hz), 5.78 (1H, d, J = 1.7Hz) | CHCl₃: 2945, 2860, 1675, 1593, 1580, 1488, 1404, 1298, 1091, 1015 |
| 62 | 0.8~1.8 (11H, m), 2.53 (1H, dd, J = 5.6 & 13.9Hz), 3.58 (1H, dd, J = 8.5 & 13.9Hz), 5.11 (1H, s), 5.72 (1H, s) | CHCl₃: 2930, 2855, 1678, 1595, 1580, 1491, 1410, 1283, 1018 |
| 63 | 0.8~1.8 (11H, m), 2.46 (1H, dd, J = 5.4 & 13.9Hz), 3.63 (1H, dd, J = 5.4 & 8.8Hz), 5.13 (1H, d, J = 1.7Hz), 5.76 (1H, d, J = 1.7Hz) | CHCl₃: 2930, 2855, 1678, 1590, 1578, 1487, 1279, 1090, 1010 |
| 64 | 2.1~2.2 (1H, m), 2.8~3.2 (1H, m), 3.6~4.0 (3H, m), 5.1~5.2 (1H, m), 5.94 (0.65H, s), 6.05 (0.35H, d, J = 2.0Hz) | CHCl₃: 1672, 1588, 1575, 1485, 1404, 1300, 1085, 1010 |
| 65 | 1.5~1.7 (2H, m), 2.7~3.15 (2H, m), 3.4~3.85 (3H, m), 5.12 (0.5H, s), 5.18 (0.5H, d, J = 2.0Hz), 5.73 (0.5H, s), 5.80 (0.5H, d, J = 2.0Hz) | CHCl₃: 3450, 2940, 1665, 1592, 1577, 1489, 1409, 1348, 1086, 1060 |
| 66 | 1.05~1.20 (3H, m), 2.0~2.3 (1H, m), 2.62~2.85 (1H, m), 3.5~4.2 (3H, m), 5.1~5.2 (1H, m), 5.93 (0.7H, s), 6.16 (0.3H, d, J = 2.0Hz) | CHCl₃: 3420, 2965, 1675, 1592, 1578, 1487, 1407, 1090, 1012 |
| 67 | 2.6~3.05 (3H, m), 3.8~4.0 (1H, m), 5.04 (1H, s), 5.28 (1H, s) | CHCl₃: 2930, 1680, 1591, 1578, 1490, 1407, 1359, 1089, 1013 |
| 68 | 2.6~3.0 (3H, m), 4.0~4.15 (1H, m), 5.06 (1H, d, J = 1.8Hz), 5.34 (1H, d, J = 1.8Hz) | CHCl₃: 2930, 1679, 1589, 1575, 1486, 1405, 1086, 1010 |
| 69 | 2.07 (3H, s), 2.9~3.1 (1H, m), 3.85~4.3 (3H, m), 5.08 (1H, s), 5.85 (1H, s) | CHCl₃: 2930, 1737, 1690, 1589, 1482, 1402, 1084 |
| 70 | 1.94 (3H, s), 2.8~2.95 (1H, m), 4.0~4.35 (3H, m), 5.12 (1H, d, J = 1.7Hz), 5.93 (1H, d, J = 1.7Hz) | CHCl₃: 2955, 1740, 1690, 1590, 1485, 1382, 1085 |
| 71 | 1.7~2.0 (2H, m), 2.00 (1.5H, s), 2.01 (1.5H, s), 2.75-2.95 (1H, m), 3.65~4.1 (3H, m), 5.07 (0.5H, s), 5.12 (0.5H, d, J = 1.7Hz), 5.73 (0.5H, s), 5.30 (0.5H, d, J = 1.7Hz) | CHCl₃: 2950, 1735, 1690, 1590, 1488, 1365, 1085 |

-continued

| Example No. | Melting point of NMR (CDCl₃) δ ppm | (a) IR(CHCl₃) [cm⁻¹] (b) IR(nujol) [cm⁻¹] (c) IR(KBr) [cm⁻¹] | |
|---|---|---|---|
| 72 | 1.15~1.20 (3H, m), 2.04 (2.3H, s), 2.09 (0.7H, s), 2.7~4.1 (2H, m), 5.05~5.20 (2H, m), 5.78 (0.23H, s), 5.95 (0.77H, s) | CHCl₃: | 2955, 1730, 1684, 1586, 1482, 1401, 1083 |
| 73 | 1.1~1.25 (3H, m), 1.81 (1.5H, s), 2.08 (1.5H, s), 2.6~4.1 (2H, m), 5.0~5.2 (2H, m), 5.85 (0.5H, d, J = 1.7Hz), 6.00 (0.5H, d, J = 1.7Hz) | CHCl₃: | 2960, 1734, 1685, 1588, 1485, 1370, 1085 |
| 74 | 2.18 (6H, s), 3.8~3.95 (1H, m), 5.06 (1H, d, J = 1.9Hz), 6.11 (1H, d, J = 1.9Hz) | CHCl₃: | 1670, 1592, 1090, 1010 |
| 75 | 2.15 (6H, s), 3.75~3.90 (1H, m), 5.10 (1H, s), 5.98 (1H, s) | CHCl₃: | 1683, 1590, 1090, 1010 |
| 76 | 140~141° C. | nujol: | 1663, 1586, 1255, 1020, 752 |
| 77 | 140~141° C. | nujol: | 1665, 1579, 1248, 1020, 754 |
| 78 | 84~87° C. | nujol: | 1690, 1587, 1301, 1102, 760 |
| 79 | 138~140° C. | nujol: | 1662, 1580, 1440, 1255, 1103, 1000, 753 |
| 80 | 81.5~82.5° C. | nujol: | 2760, 1660, 1580, 1419, 1276, 1220, 1063, 847 |
| 81 | 73~74° C. | nujol: | 1662, 1647, 1577, 1420, 1327, 1305, 1165, 1039, 1020 |
| 82 | 0.98 (3H, t, J = 7.3Hz), 2.15 (6H, s), 2.35~2.55 (1H, m), 3.7~3.9 (1H, m), 4.0~4.1 (1H, m), 5.86 (1H, d, J = 1.7Hz) | CHCl₃: | 1670, 1578, 1355, 1010 |
| 83 | 65~66° C. | nujol: | 1659, 1585, 1419, 1291, 1260, 1021 |
| 84 | 0.94 (3H, t, J = 6.6Hz), 2.15 (6H, s), 2.4~2.52 (1H, m), 2.64~2.74 (1H, m), 3.75~3.85 (1H, m), 4.00~4.06 (1H, m), 5.86 (1H, d, J = 2.0Hz) | CHCl₃: | 2930, 2790, 1665, 1580, 1360, 1098 |
| 85 | 0.92 (3H, t, J = 7.0Hz), 2.13 (6H, s), 2.37~2.54 (1H, m), 2.64~2.74 (1H, m), 3.75~3.85 (1H, m), 3.95~4.0 (1H, m), 5.85 (1H, s) | CHCl₃: | 2920, 2780, 1665, 1579, 1357, 1096 |
| 86 | 0.90 (3H, t, J = 7.0Hz), 2.15 (6H, s), 2.39~2.51 (1H, m), 2.64~2.74 (1H, m), 3.75~3.85 (1H, m), 4.0~4.06 (1H, m), 5.86 (1H, d, J = 2.0Hz) | CHCl₃: | 2920, 2770, 1662, 1577, 1358 |
| 87 | 0.89 (3H, t, J = 7.0Hz), 21.3 (6H, s), 2.38~2.54 (1H, m), 2.64~2.74 (1H, m), 3.75~3.85 (1H, m), 3.95~4.00 (1H, m), 5.84 (1H, s) | CHCl₃: | 2920, 2770, 1662, 1577, 1358 |
| 88 | 0.89 (3H, t, J = 6.7Hz), 2.15 (6H, s), 2.35~2.55 (1H, m), 2.6~2.8 (1H, m), 3.7~3.9 (1H, m), 4.0~4.1 (1H, m), 5.86 (1H, d, J = 2.0Hz) | CHCl₃: | 2930, 1664, 1578, 1358, 1295 |
| 89 | 0.88 (3H, t, J = 6.7Hz), 2.13 (6H, s), 2.35~2.55 (1H, m), 2.6~2.8 (1H, m), 3.7~3.9 (1H, m), 3.9~4.05 (1H, m), 5.84 (1H, s) | CHCl₃: | 2920, 1660, 1578, 1359, 1296, 1097 |
| 90 | 0.88 (3H, t, J = 6.7Hz), 2.15 (6H, s), 2.35~2.55 (1H, m), 2.6~2.8 (1H, m), 3.75~3.90 (1H, m), 4.0~4.1 (1H, m), 5.86 (1H, d, J = 1.7Hz) | CHCl₃: | 2930, 1665, 1580, 1410, 1355, 1295, 1020 |
| 91 | 0.88 (3H, t, J = 6.8Hz), 2.13 (6H, s), 2.35~2.55 (1H, m), 2.6~2.8 (1H, m), 3.75~3.85 (1H, m), 3.9~4.0 (1H, m), 5.84 (1H, s) | CHCl₃: | 2915, 2860, 1665, 1575, 1355, 1290, 1093 |
| 92 | 0.88 (3H, t, J = 6.7Hz), 2.16 (6H, s), 2.40~2.55 (1H, m), 2.60~2.75 (1H, m), 3.75~3.85 (1H, m), 4.0~4.05 (1H, m), 5.85 (1H, d, J = 2.0Hz) | CHCl₃: | 2920, 2855, 1670, 1577, 1358, 1295 |

| Example No. | Melting point of NMR (CDCl₃) δ ppm | (a) IR(CHCl₃) [cm⁻¹]<br>(b) IR(nujol) [cm⁻¹]<br>(c) IR(KBr) [cm⁻¹] |
|---|---|---|
| 93 | 0.87 (3H, t, J = 6.7Hz), 2.15 (6H, s), 2.35~2.55 (1H, m), 2.6~2.8 (1H, m), 3.75~3.85 (1H, m), 3.9~4.0 (1H, m), 5.84 (1H, s) | CHCl₃: 2920, 2855, 1670, 1578, 1355 |
| 94 | 0.88 (3H, t, J = 6.7Hz), 2.16 (6H, s), 2.40~2.52 (1H, m), 2.60~2.75 (1H, m), 3.75~3.85 (1H, m), 4.0~4.05 (1H, m), 5.85 (1H, d, J = 1.7Hz) | CHCl₃: 2920, 2855, 1655, 1577, 1350 |
| 95 | 0.88 (3H, t, J = 6.6Hz), 2.16 (6H, s), 2.39~2.50 (1H, m), 2.64~2.75 (1H, m), 3.76~3.85 (1H, m), 3.95-4.00 (1H, m), 5.84 (1H, s) | CHCl₃: 2920, 2850, 1665, 1576, 1355, 1290 |
| 96 | 0.88 (3H, t, J = 6.6Hz), 2.16 (6H, s), 2.40~2.52 (1H, m), 2.63~2.74 (1H, m), 3.75~3.85 (1H, m), 4.0~4.05 (1H, m), 5.85 (1H, d, J = 2.0Hz) | CHCl₃: 2920, 2860, 1663, 1577, 1356, 1290, 1090 |
| 97 | 0.88 (3H, t, J = 6.8Hz), 2.14 (6H, s), 2.39~2.49 (1H, m), 2.63~2.74 (1H, m), 3.75~3.85 (1H, m), 3.95~4.00 (1H, m), 5.84 (1H, s) | CHCl₃: 2915, 2855, 1670, 1575, 1358, 1295, 1092 |
| 98 | 0.88 (3H, t, J = 6.7Hz), 2.16 (6H, s), 2.40~2.52 (1H, m), 2.63~2.75 (1H, m), 3.75~3.85 (1H, m), 4.00~4.05 (1H, m), 5.85 (1H, d, J = 2.0Hz) | CHCl₃: 2910, 2855, 1660, 1579, 1355, 1295, 1095 |
| 99 | 0.88 (3H, t, J = 6.6Hz), 2.14 (6H, s), 2.39~3.49 (1H, m), 2.63~2.74 (1H, m), 3.75~3.85 (1H, m), 3.95~4.00 (1H, m), 5.84 (1H, s) | CHCl₃: 2920, 2850, 1670, 1575, 1355, 1290 |
| 100 | 35.5~36.5° C. | nujol: 1683, 1290, 1017, 705 |
| 101 | 71.5~72.5° C. | nujol: 1654, 1577, 1420, 1268, 712 |
| 102 | 40~41° C. | nujol: 1685, 1573, 1415, 1298, 1155, 710 |
| 103 | 59~60° C. | nujol: 1653, 1575, 1420, 1265, 1145, 710 |
| 104 | 45~46° C. | nujol: 1685, 1577, 1298, 1260, 1154, 710 |
| 105 | 76.5~77.5° C. | nujol: 1652, 1573, 1418, 1300, 712 |
| 106 | 42~44° C. | nujol: 1687, 1672, 1300, 1021 |
| 107 | 65~66° C. | nujol: 1650, 1577, 1142, 1020 |
| 108 | 52.5~53.5° C. | nujol: 1685, 1578, 1295, 1259 |
| 109 | 81~82° C. | nujol: 1652, 1577, 1420, 1142, 713 |
| 110 | 68~70° C. | nujol: 1690, 1578, 1300, 1260, 1159, 1020 |
| 111 | 63~64° C. | nujol: 1655, 1579, 1421, 1270, 1144, 713 |
| 112 | 57.5~58.5° C. | nujol: 1690, 1575, 1300, 1023, 710 |
| 113 | 84.5~85.5° C. | nujol: 1652, 1575, 1419, 1301, 1262, 1140, 709 |
| 114 | 53~56° C. | nujol: 1684, 1572, 1410, 709 |
| 115 | 73.5~75° C. | nujol: 1653, 1578, 1420, 1265, 1220, 710 |
| 116 | 4.07 (1H, dq, J = 1.7 & 7.0Hz), 5.65 (1H, d, J = 1.7Hz) | CHCl₃: 2925, 2810, 1670, 1573, 1445, 1113 |
| 117 | 3.96 (1H, dq, J = 7.0Hz), 5.66 (1H, s) | CHCl₃: 2920, 2805, 1665, 1572, 1445, 1110 |
| 118 | 0.97 (3H, t, J = 7.3Hz), 2.16 (6H, s), 3.6~3.75 (1H, m), 4.0~4.1 (1H, m), 5.63 (1H, d, J = 2.0Hz) | CHCl₃: 2900, 1663, 1575 |
| 119 | 0.97 (3H, t, J = 7.3Hz), 2.22 (6H, s), 3.55~3.70 (1H, m), 3.9~4.0 (1H, m), 5.68 (1H, s) | CHCl₃: 2860, 1660, 1410, 1300 |
| 120 | 0.89 (3H, t, J = 6.6Hz), 2.21 (6H, s), 3.6~3.75 (1H, m), 4.0~4.1 (1H, m), 5.63 (1H, d, J = 2.0Hz) | CHCl₃: 2910, 2860, 1665 |
| 121 | 0.88 (3H, t, J = 6.6Hz), 2.13 (6H, s), 3.55-3.70 (1H, m), | CHCl₃: 2900, 2870, 1660, 1579 |

-continued

| Example No. | Melting point of NMR (CDCl$_3$) δ ppm | (a) IR(CHCl$_3$) [cm$^{-1}$]<br>(b) IR(nujol) [cm$^{-1}$]<br>(c) IR(KBr) [cm$^{-1}$] |
|---|---|---|
| 122 | 3.9~4.0 (1H, m), 5.65 (1H, s) 2.15 (6H, s), 4.0~4.07 (1H, m), 5.63 (1H, d, J = 1.7Hz) | CHCl$_3$: 2910, 2855, 1670, 1577, 1300, 1020 |
| 123 | 2.13 (6H, s), 3.94 (1H, dd, J = 3.7 & 9Hz), 5.65 (1H, s) | CHCl$_3$: 2930, 2860, 1670, 1580, 1300, 1020 |
| 124 | 77~78° C. | nujol: 1675, 1586, 1512, 1253, 1021 |
| 125 | 55~56° C. | nujol: 1673, 1590, 1414, 1267, 1239, 1025, 800 |
| 126 | 63~64° C. | nujol: 1655, 1576, 1421, 1269, 719 |
| 127 | 73~74° C. | nujol: 1652, 1581, 1424, 1310, 1028, 715 |
| 128 | 65.5~66.5° C. | nujol: 1659, 1585, 1400, 1302, 1269, 1200, 1129, 703 |
| 129 | 0.85~0.9 (3H, m), 2.16 (4H, s), 2.17 (2H, s), 3.0~3.75 (1H, m), 3.9~4.0 (0.67H, m) 4.0~4.1 (0.33H, m), 5.59, (0.33H, d, J = 2.0Hz), 5.62 (0.67H, s) | CHCl$_3$: 2840, 1655, 1408, 1350 |
| 130 | 0.88 (3H, t, J = 6.7Hz), 0.97 (6H, t, J = 7.1Hz), 3.65~3.8 (1H, m), 3.95~4.05 (1H, m), 5.89 (1H, d, J = 2.0Hz) | CHCl$_3$: 2850, 1660 |
| 131 | 0.87 (3H, t, J = 6.7Hz), 0.95 (6H, t, J = 7.1Hz), 3.6~3.75 (1H, m), 3.9~4.0 (1H, m), 5.90 (1H, m) | CHCl$_3$: 2880, 1658 |
| 132 | 0.88 (3H, t, J = 6.6Hz), 1.06 (3H, t, J = 7.1Hz), 3.7~3.9 (1H, m), 4.0~4.1 (1H, m), 5.79 (1H, d, J = 1.7Hz) | CHCl$_3$: 2860, 1665 |
| 133 | 0.88 (3H, t, J = 6.7Hz), 1.05 (3H, t, J = 7.1Hz), 3.65~3.80 (1H, m), 3.95~4.0 (1H, m), 5.81 (1H, s) | CHCl$_3$: 2900, 2850, 1663 |
| 134 | 0.85~0.9 (3H, m), 2.6~2.8 (2H, m), 3.75~4.1 (2H, m), 5.88~5.86 (1H, m) | CHCl$_3$: 2850, 1685, 1350 |
| 135 | 2.83~2.88 (4H, m), 3.66~3.78 (4H, m), 3.94~3.99 (0.5H, m), 3.99~4.03 (0.5H, m), 5.85 (0.5H, d, J = 1.9Hz), 5.86 (0.5H, s) | CHCl$_3$: 2850, 1660 |
| 136 | 3.63~3.76 (2H, m), 3.96~4.01 (0.5H, m), 4.01~4.08 (0.5H, m), 5.73 (0.5H, d, J = 1.7Hz), 5.76 (0.5H, s) | CHCl$_3$: 2850, 1660, 1577, 1403 |
| 137 | 2.17 (3H, s), 5.90 (0.5H, d, J = 1.7Hz), 5.91 (0.5H, s) | CHCl$_3$: 2855, 1670, 1630 |
| 138 | 0.87 (6H, d, J = 6.6Hz), 0.95 (3H, d, J = 6.4Hz), 2.15 (6H, s), 3.75~3.85 (1H, m), 3.99~4.05 (1H, m), 5.86 (1H, d, J = 2.0Hz) | CHCl$_3$: 2855, 1660, 1578, 1358 |
| 139 | 2.15 (6H, s), 3.75~3.85 (1H, m), 4.0~4.05 (1H, m), 5.14~5.26 (2H, m), 5.85 (1H, d, J = 2.0Hz), 5.8~6.0 (1H, m) | CHCl$_3$: 2870, 1660, 1578, 1403, 1352 |
| 140 | 3.11~3.44 (2H, m), 3.67~3.76 (1H, m), 4.03~4.35 (1H, m), 5.49 (1H, d, J = 2.0Hz) | CHCl$_3$: 2770, 1660, 1577 |
| 141 | 2.15 (6H, s), 3.75~3.85 (1H, m), 4.0~4.05 (1H, m), 5.86 (1H, d, J = 1.7Hz) | CHCl$_3$: 2870, 1655, 1578, 1405, 1353 |
| 142 | 2.5~3.0 (3H, m), 3.6~4.0 (3H, m), 3.85 (3H, s), 3.88 (3H, s), 5.23 (1H, d, J = 1.5Hz) | CHCl$_3$: 2940, 2845, 1675, 1595, 1440, 1360, 1020 |
| 143 | 0.99~1.08 (3H, m), 1.59~1.67 (3H, m), 3.6~3.85 (1H, m), 3.9~4.05 (0.6H, m), 4.05–4.20 (0.4H, m), 5.61 (0.4H, d, J = 1.7Hz), 5.63 (0.6H, s) | CHCl$_3$: 2930, 1670, 1585, 1575, 1445, 1419, 1120 |
| 144 | 1.63 (3H, d, J = 7.1Hz), 3.0~3.2 (1H, m), 4.0~4.2 (1H, m), 4.4~4.6 (1H, m), 5.0~5.3 (2H, m), 5.57 (1H, d, J = 2Hz), 5.6~5.8 (1H, m) | CHCl$_3$: 1674, 1590, 1579, 1120 |

-continued

| Example No. | Melting point of NMR (CDCl$_3$) δ ppm | (a) IR(CHCl$_3$) [cm$^{-1}$]<br>(b) IR(nujol) [cm$^{-1}$]<br>(c) IR(KBr) [cm$^{-1}$] | |
|---|---|---|---|
| 145 | 46~48° C. | nujol: | 1650, 1595, 1580, 1275, 1180, 1021 |
| 146 | 1.63 (3H, d, J = 7.1Hz), 3.26~3.34 (1H, m), 4.06~4.12 (1H, m), 4.61~4.70 (1H, m), 5.80 (1H, d, J = 1.7Hz) | CHCl$_3$: | 3405, 1680, 1578, 1400, 1348 |
| 147 | 1.67 (3H, d, J = 7.1Hz), 3.23~3.30 (1H, m), 3.96~4.05 (1H, m), 4.61~4.69 (1H, m), 5.80 (1H, s) | CHCl$_3$: | 3405, 1680, 1578, 1400, 1350 |
| 148 | 111~111.5° C. | nujol: | 1660, 1580, 1418, 1305, 1149, 1025, 1005 |
| 149 | 107~107.5° C. | nujol: | 1664, 1649, 1579, 1420, 1305, 1157 |
| 150 | 92~93° C. | nujol: | 1662, 1576, 1512, 1420, 1269, 1239, 1142, 1025 |
| 151 | 92~94° C. | nujol: | 1658, 1585, 1511, 1416, 1260, 1140, 1021 |
| 152 | 1.59~1.67 (3H, m), 3.26 (1.8H, s), 3.29 (1.2H, s), 5.63 (0.4H, d, J = 1.7Hz), 5.65 (0.6H, s) | CHCl$_3$: | 2920, 2860, 1760, 1572, 1440, 1300, 1111 |
| 153 | 104~106° c. | nujol: | 1677, 1650, 1580, 1299, 1145, 1025, 710 |
| 154 | 100~101° C. | nujol: | 1681, 1656, 1591, 1580, 1140 |
| 155 | 1.0~2.4 (5H, m), 2.73 (1H, s), 2.74 (1H, s), 3.9~4.2 (1H, m), 5.48 (0.7H, d, J = 2.0Hz), 5.50 (0.3H, s) | CHCl$_3$: | 2950, 1670, 1590, 1578, 1388, 1301, 1020 |
| 156 | 0.9~2.4 (7H, m), 2.72 (1.2H, s), 2.75 (1.8H, s), 3.9~4.1 (1H, m), 5.47 (0.6H, d, J = 2.0Hz), 5.49 (0.4H, s) | CHCl$_3$: | 2960, 2940, 1670, 1595, 1581, 1392, 1015 |
| 157 | 0.9~2.4 (8H, m), 2.72 (3H, s), 4.1~4.3 (1H, m) | CHCl$_3$: | 2955, 1672, 1590, 1579, 1305 |
| 158 | 0.8~2.5 (8H, m), 5.47 (0.5H, d, J = 2.0Hz), 5.49 (0.5H, s) | CHCl$_3$: | 2950, 1674, 1589, 1578 |
| 159 | 0.8~2.3 (11H, m), 2.72 (0.3H, s), 2.74 (2.7H, s), 3.9~4.1 (1H, m), 5.47 (0.9H, d, J = 1.7Hz), 5.49 (0.1H, s) | CHCl$_3$: | 2930, 2855, 1670, 1590, 1578, 1390, 1120, 1009 |
| 160 | 0.8~2.3 (13H, m), 2.72 (0.6H, s), 2.74 (2.4H, s), 3.9~4.1 (1H, m), 5.47 (0.8H, d, J = 2.0Hz), 5.49 (0.2H, s) | CHCl$_3$: | 2925, 2855, 1670, 1589, 1578, 1390, 1300, 1020 |
| 161 | 0.8~2.4 (19H, m), 2.72 (1H, s), 2.74 (2H, s), 3.9~4.1 (1H, m), 5.47 (0.74H, d, J = 2.0Hz), 5.49 (0.3H, s) | CHCl$_3$: | 2920, 2850, 1670, 1589, 1576, 1300, 1009 |
| 162 | 52.5~53° C. | nujol: | 1663, 1578, 1420, 1020 |
| 163 | 67.5~68.5° C. | nujol: | 1660, 1575, 1408, 1391, 1325, 1250, 708 |
| 164 | 0.8~2.4 (21H, m), 2.72 (1H, s), 2.74 (2H, s), 3.9~4.1 (1H, m), 5.47 (0.7H, d, J = 2.0Hz), 5.49 (0.3H, s) | CHCl$_3$: | 2920, 2850, 1670, 1590, 1578, 1300, 1010 |
| 165 | 3.86 (3H, s), 3.87 (3H, s), 5.17 (1H, d, J = 1.7Hz) | CHCl$_3$: | 2930, 2860, 1670, 1590, 1360 |
| 166 | 3.84 (3H, s), 3.87 (3H, s), 5.20 (1H, s) | CHCl$_3$: | 2920, 2850, 1670, 1589, 1138, 1018 |
| 167 | 57~58° C. | nujol: | 1724, 1693, 1579, 1432, 1292, 1023, 715 |
| 168 | 47~48° C. | nujol: | 1742, 1683, 1577, 1420, 1295, 1210, 1025, 709 |
| 169 | 55~56° C. | nujol: | 1739, 1660, 1550, 1214 |
| 170 | 46~47° C. | nujol: | 1740, 1667, 1657, 1582, 1191, 1020 |
| 171 | 55~56° C. | nujol: | 1673, 1590, 1414, 1267, 1239, 1025, 800 |
| 172 | 77~78° c. | nujol: | 1675, 1586, 1512, 1253, 1021 |
| 173 | 2.71 (3H, s), 4.01 (0.85H, dd, J = 3.5 & 11.3Hz), 4.05~4.2 (0.15H, m), 5.4~5.5 (1H, m) | nujol: | 1665, 1585, 1570, 1310, 1265, 1025 |
| 174 | 78~79° C. | nujol: | 1660, 1578, 1262, 1025, 735 |
| 175 | 0.9~1.1 (6H, m), 1.1~2.1 (8H, m), 2.69 (3H, s), 5.39 (1H, s) | CHCl$_3$: | 2950, 2930, 1673, 1589, 1578, 1388, 901 |
| 176 | 2.72 (0.75H, s), 2.75~2.25H, | CHCl$_3$: | 2900, 1675, 1590, 1580, |

-continued

| Example No. | Melting point of NMR (CDCl₃) δ ppm | (a) IR(CHCl₃) [cm⁻¹]<br>(b) IR(nujol) [cm⁻¹]<br>(c) IR(KBr) [cm⁻¹] | |
|---|---|---|---|
| | s), 4.03~4.09 (0.25H, m), 4.10~4.17 (0.75H, m), 5.46 (0.75H, d, J = 2.0Hz), 5.50 (0.25H, s) | | 1390, 1350, 1300 |
| 177 | 133~135° C. | nujol: | 3220, 1679, 1581, 1315, 1024, 721 |
| 178 | 139~142° C. | nujol: | 1700, 1482, 1085, 800, 705 |
| 179 | 278~281° C. | nujol: | 1705, 1495, 1090, 1060, 705 |
| 180 | 86~88° C. | nujol: | 1690, 1495, 1410, 1060 |
| 181 | 0.85 (3H, t, J = 7.4Hz), 2.60~2.80 (1H, m), 3.55~3.80 (1H, m), 5.09 (0.5H, s), 5.13 (0.5H, d, J = 1.9Hz), 5.72 (0.5H, s), 5.79 (0.5H, d, J = 1.9Hz) | CHCl₃: | 1680, 1590, 1580, 1490, 1410, 1090, 1015 |
| 182 | 153~154° C. | nujol: | 1674, 1575, 1492, 1413, 1085, 1068, 1057, 817 |
| 183 | 2.40~2.60 (1H, m), 3.50~3.65 (1H, m), 5.12 (0.5H, s), 5.14 (0.5H, d, J = 1.7Hz), 5.73 (0.5H, s), 5.77 (0.5H, d, J = 1.7Hz) | CHCl₃: | 1675, 1590, 1580, 1490, 1405, 1085, 1010 |
| 184 | 158~160° C. | nujol: | 1680, 1420, 1275, 1090, 1050, 810, 700 |
| 185 | 110~113° C. | nujol: | 1665, 1495, 1405, 1090 |
| 186 | 168~169° c. | nujol: | 1695, 1085, 1060, 1020, 810, 710 |
| 187 | 152~154° C. | nujol: | 1680, 1495, 1410, 1050, 820, 710 |
| 188 | 3.70~3.80 (1H, m), 4.95~5.08 (1H, m), 5.10 (0.5H, s), 5.16 (0.5H, d, J = 1.7Hz), 5.61 (0.5H, s), 5.68 (0.5H, d, J = 1.7Hz), 6.10~6.15 (1H, m), 6.25~6.35 (1H, m) | CHCl₃: | 1690, 1495, 1405, 1090, 1015 |
| 189 | 131~133° C. | nujol: | 1690, 1592, 1493, 1405, 1148, 1086, 1069 |
| 190 | 149~152° c. | nujol: | 1690, 1580, 1060, 1040, 1000, 710 |
| 191 | 1.08~1.15 (6H, m), 2.75~2.90 (1H, m), 3.70~3.85 (1H, m), 5.06 (0.5H, s), 5.11 (0.5H, d, J = 1.7Hz), 5.82 (0.5H, s), 5.87 (0.5H, d, J = 1.7Hz) | CHCl₃: | 1675, 1490, 1405, 1020, 1090 |
| 192 | 121~123° C. | nujol: | 1691, 1677, 1571, 1490, 1412, 1255, 1052, 821 |
| 193 | 1.10~1.30 (6H, m), 2.65~2.75 (1H, m), 4.53~4.65 (1H, m), 5.08 (0.4H, d, J = 1.8Hz), 5.11 (0.6H, s), 6.03 (0.6H, s), 6.11 (0.4H, d, J = 1.8Hz) | CHCl₃: | 1690, 1490, 1405, 1280, 1120 |
| 194 | 163~165° C. | nujol: | 1695, 1510, 1230, 1060, 810, 700 |
| 195 | 1.61 (3H, d, J = 6.8Hz), 2.16 (6H, s), 3.8~3.9 (1H, m), 3.95~4.15 (1H, m), 5.88 (1H, d, J = 1.7Hz) | CHCl₃: | 2930, 1690, 1580, 1359, 1149 |
| 196 | 71.5~72.5° C. | nujol: | 1659, 1573, 1415, 1283, 1100 |
| 197 | 117~120° C. | nujol: | 1685, 1594, 1575, 1493, 1065 |
| 198 | 155~160° C. | nujol: | 1686, 1585, 1489, 1388, 1099 |
| 199 | 132~135° C. | nujol: | 1697, 1587, 1252, 1073, 760 |
| 200 | 132~136° C. | nujol: | 1675, 1589, 1258, 1097, 781 |
| 201 | 140~142° C. | nujol: | 1700, 1592, 1268, 1067, 823, 703 |
| 202 | 93~95° C. | | |
| 203 | HCl salt 88~90° C. | | |
| 204 | HCl salt 79~82° C. | | |
| 205 | HCl salt 133~135° C. | nujol: | 1675, 1492, 1087, 1014 |
| 206 | 4.67 (0.1H, s), 4.77 (0.9H, s), 5.57 (0.9H, s), 5.67 (0.1H, s) | nujol: | 1688, 1599, 1580, 1498, 1090, 1071, 821 |
| 207 | HCl salt | nujol: | 1670, 1540, 1485, 1081, |

| Example No. | Melting point of NMR (CDCl₃) δ ppm | (a) IR(CHCl₃) [cm⁻¹]<br>(b) IR(nujol) [cm⁻¹]<br>(c) IR(KBr) [cm⁻¹] | |
|---|---|---|---|
| | 93~95° C. | | 1010, 802 |
| 208 | 127~129° C. | nujol: | 1692, 1579, 1492, 1258, 1087, 1072, 1058, 811, 704 |
| 209 | 87~90° C. | nujol: | 1692, 1577, 1065, 751 |
| 210 | 113~115° C. | nujol: | 1681, 1601, 1579, 1492, 1257, 1058, 1028, 755 |
| 211 | 138~140° C. | nujol: | 1662, 1580, 1440, 1255, 1103, 1000, 753 |
| 212 | 171~174° C. | nujol: | 1690, 1630, 1580, 1230, 1100, 990, 800 |
| 213 | 186~189° C. | nujol: | 1720, 1630, 1595, 1240, 1060, 1005, 800, 710 |
| 214 | 138~140° C. | nujol: | 1690, 1630, 1590, 1260, 1240, 1100, 1000, 790 |
| 215 | 153~154° C. | nujol: | 1700, 1640, 1600, 1300, 1280, 1240, 1070, 1000, 800 |
| 216 | 125~126° C. | nujol: | 1690, 1620, 1600, 1580, 1290, 1150, 970 |
| 217 | 164~166° C. | nujol: | 1690, 1620, 1600, 1510, 1070, 965, 850 |
| 218 | 152~153° C. | nujol: | 1670, 1610, 1505, 1140, 1085, 965, 860 |
| 219 | 119~123° C. | nujol: | 1690, 1620, 1610, 1510, 1280, 1260, 845, 715 |
| 220 | 115~118° C. | nujol: | 1680, 1610, 1510, 1430, 1390, 1230, 835, 825, 705 |
| 221 | 135~138° C. | nujol: | 1675, 1590, 1500, 1470, 1385, 1220, 810, 710 |
| 222 | 112~114° C. | nujol: | 1680, 1585, 1575, 1490, 1390, 1245, 1090, 760, 705 |
| 223 | 161~163° C. | nujol: | 1680, 1580, 1485, 1380, 1255, 1090, 790, 760, 710 |
| 224 | 155~159° C. | nujol: | 1690, 1510, 1465, 1380, 1060, 820, 705 |
| 225 | 146~148° C. | nujol: | 1690, 1510, 1460, 1375, 1220, 1090, 1055, 835, 710 |
| 226 | 70~100° C. | nujol: | 1680, 1260, 1235 |
| 227 | 66~74° C. | nujol: | 1670, 1600, 1505, 1410, 1285, 1220, 1150, 795 |
| 228 | 160~161° C. | nujol: | 1690, 1600, 1515, 1460, 1415, 1380, 1225, 1060, 840, 705 |
| 229 | 71~72° C. | nujol: | 1660, 1590, 1500, 1460, 1415, 1370, 1290, 1220, 1020, 810, 705 |
| 230 | 155~156° C. | nujol: | 1680, 1510, 1450, 1375, 1220, 1070 |
| 231 | HCl salt<br>87~102° C. | nujol: | 1670, 1600, 1510, 1460, 1410, 1220, 1160, 800 |
| 232 | 152~154° C. | nujol: | 1710, 1640, 1620, 1535, 1480, 1440, 1260, 1190, 1085, 860, 740 |
| 233 | HCl salt<br>70~72° C. | KBr: | 1680, 1605, 1550, 1510, 1415, 1225, 1160, 1065, 810, 680 |
| 234 | 131~132° C. | nujol: | 1680, 1600, 1510, 1460, 1365, 1225, 1065, 815, 710 |
| 235 | HCl salt<br>58~63° C. | KBr: | 1680, 1600, 1550, 1510, 1415, 1220, 1155, 810, 680, 610 |
| 236 | 155~158° C. | nujol: | 1680, 1600, 1585, 1575, 1510, 1460, 1410, 1375, 1225, 1080, 825, 710 |
| 237 | HCl salt<br>61~65° C. | KBr: | 1680, 1550, 1495, 1460, 1420, 1380, 1290, 1230, 1110, 765, 685 |
| 238 | 138~140° C. | nujol: | 1690, 1580, 1495, 1460, 1410, 1375, 1230, 1070, 760, 710 |
| 239 | HCl salt<br>67~70° C. | KBr: | 1680, 1550, 1495, 1420, 1380, 1290, 1230, 1110, 890, 760 |
| 240 | 145~146° C. | nujol: | 1690, 1585, 1495, 1460, 1410, 1370, 1260, 1070, 760, 710 |
| 241 | 127~130° C. | nujol: | 1670, 1580, 1490, 1460, 1415, 1365, 1270, 1225, 1190, 1120, 1105, 1025, 770 |
| 242 | 167~170° C. | nujol: | 1680, 1495, 1460, 1410, |

-continued

| Example No. | Melting point of NMR (CDCl₃) δ ppm | (a) IR(CHCl₃) [cm⁻¹]<br>(b) IR(nujol) [cm⁻¹]<br>(c) IR(KBr) [cm⁻¹] | |
|---|---|---|---|
| | | | 1375, 1255, 1065, 1020, 755, 710 |
| 243 | 106~127° C. | | |
| 244 | 140~142° C. | nujol: | 1690, 1330, 1165, 1130, 1070, 1025, 850, 830, 720 |
| 245 | 159.5~161.5° C. | nujol: | 1675, 1580, 1325, 1170, 1130, 1070, 1020, 1005, 835, 825, 720 |
| 246 | 115.5~117.2° C. | nujol: | 1685, 1340, 1170, 1135, 1075, 1025, 840, 820, 720 |
| 247 | HCl salt 70~73° C. | nujol: | 1680, 1630, 1610, 1550, 1490, 1450, 1410, 1380, 1290, 1065, 1010, 890, 820, 760 |
| 248 | 145~147° C. | nujol: | 1680, 1610, 1580, 1490, 1450, 1410, 1370, 1315, 1250, 1230, 1150, 1060, 1040, 880, 820, 775 |
| 249 | HCl salt 78~80° C. | KBr: | 1680, 1630, 1550, 1490, 1450, 1420, 1380, 1270, 1230, 1110, 1090, 1030, 890, 820, 760 |
| 250 | 150~152° C. | nujol: | 1690, 1580, 1500, 1460, 1410, 1380, 1340, 1315, 1260, 1240, 1210, 1160, 1120, 1080, 1025, 890, 830, 820, 765 |
| 251 | HCl salt 61~64° C. | KBr: | 1690, 1630, 1610, 1580, 1550, 1490, 1470, 1440, 1410, 1380, 1280, 1185, 1110, 1090, 990, 890, 810, 800, 760 |
| 252 | 137~140° C. | nujol: | 1690, 1640, 1580, 1495, 1460, 1410, 1375, 1315, 1260, 1235, 1150, 1090, 1075, 1020, 810, 760 |
| 253 | HCl salt 71~76° C. | KBr: | 1680, 1630, 1610, 1580, 1550, 1490, 1415, 1380, 1260, 1180, 1110, 1030, 890, 810, 800, 760 |
| 254 | 138~140° C. | nujol: | 1690, 1620, 1590, 1580, 1500, 1460, 1410, 1380, 1320, 1270, 1240, 1165, 1150, 1095, 1060, 960, 815, 750, 735, 720, 710 |
| 255 | HCl salt 66~71° C. | KBr: | 1690, 1630, 1610, 1550, 1490, 1470, 1430, 1410, 1380, 1260, 1170, 1105, 1030, 890, 810, 760 |
| 256 | 137~139° C. | nujol: | 1700, 1685, 1585, 1495, 1460, 1375, 1230, 1170, 1095, 1070, 1045, 1025, 820, 760, 710 |
| 257 | HCl salt 59~63° C. | KBr: | 1680, 1600, 1550, 1510, 1470, 1440, 1410, 1280, 1210, 1160, 1095, 940, 810, 680 |
| 258 | 140~143° C. | nujol: | 1685, 1510, 1460, 1405, 1375, 1230, 1160, 1070, 1060, 1020, 935 |
| 259 | HCl salt 81~93° C. | KBr: | 1680, 1600, 1550, 1510, 1470, 1415, 1380, 1260, 1220, 1160, 810, 705, 680 |
| 260 | 150~151° C. | nujol: | 1690, 1610, 1510, 1460, 1380, 1255, 1230, 1160, 1070, 1030, 955, 740, 710 |
| 261 | HCl salt 75~80° C. | KBr: | 1680, 1600, 1550, 1510, 1470, 1430, 1410, 1375, 1220, 1160, 1100, 810, 680 |
| 262 | 144~147° C. | nujol: | 1690, 1600, 1510, 1460, 1380, 1220, 1070, 1045, 850, 830, 710 |
| 263 | 88~90° C. | nujol: | 1700, 1610, 1585, 1515, 1470, 1445, 1420, 1380, 1335, 1275, 1235, 1160, 1125, 1050, 1030, 850, 830 |
| 264 | HCl salt 78~80° C. | KBr: | 1740, 1690, 1635, 1550, 1490, 1430, 1375, 1210, 1090, 1015, 810 |

| Example No. | Melting point of NMR (CDCl₃) δ ppm | (a) IR(CHCl₃) [cm⁻¹]<br>(b) IR(nujol) [cm⁻¹]<br>(c) IR(KBr) [cm⁻¹] |
|---|---|---|
| 265 | 130~132° C. | nujol: 1750, 1715, 1695, 1600, 1580, 1500, 1470, 1380, 1220, 1090, 1065, 1020 |
| 266 | 68~74° C. | nujol: 1680, 1600, 1495, 1470, 1380, 1175, 1090, 1015, 945, 810, 710 |
| 267 | 135~141° C. | nujol: 1625, 1590, 1490, 1470, 1380, 1090, 1070, 810, 710 |
| 268 | 45~47° C. | |
| 269 | 61~64° C. | CDCl₃: 1750, 1690, 1590, 1575, 1490, 1440, 1410, 1360, 1290, 1220, 1180, 1090, 1015, 750, 710 |
| 270 | 69~73° C. | nujol: 1760, 1690, 1590, 1575, 1490, 1450, 1380, 1290, 1220, 1090, 1065, 1020, 710 |
| 271 | 117~121° C. | nujol: 1750, 1695, 1595, 1580, 1495, 1470, 1420, 1380, 1355, 1300, 1230, 1215, 1190, 1090, 1030, 1020, 970 |
| 272 | 119~120° C. | nujol: 1755, 1710, 1600, 1580, 1500, 1470, 1440, 1385, 1280, 1205, 1165, 1095, 1070, 1020, 945 |
| 273 | 121~125° C. | CDCl₃: 1680, 1600, 1560, 1495, 1425, 1380, 1290, 1263, 1220, 1090, 1020, 760 |
| 274 | 2HCl salt 72~78° C. | nujol: 1680, 1550, 1470, 1380, 1210, 1170, 1090, 1015, 975, 810, 715 |

Compounds represented by the following general formula having the structure as shown in Table below may be produce in the same manner as of examples 1-274 above:

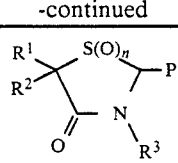

| Ex. No. | n | R¹— | R²— | R³— | P |
|---|---|---|---|---|---|
| 275 | 0 | 4-Cl-C₆H₄— | CH₃— | CH₃— | 2-pyridyl |
| 276 | 1 | " | " | " | " |
| 277 | 0 | " | H | " | 6-methyl-2-pyridyl |
| 278 | 1 | " | " | " | " |
| 279 | 0 | " | " | " | 2-methyl-pyridyl |
| 280 | 1 | " | " | " | " |
| 281 | 0 | " | " | " | 2-chloro-pyridyl |
| 282 | 1 | " | " | " | " |
| 283 | 0 | " | " | " | 6-chloro-pyridyl |
| 284 | 1 | " | " | " | " |
| 285 | 0 | 4-F-C₆H₄— | CH₃— | " | 2-pyridyl |
| 286 | 1 | " | " | " | " |
| 287 | 0 | " | H— | " | 6-methyl-2-pyridyl |
| 288 | 1 | " | " | " | " |

-continued

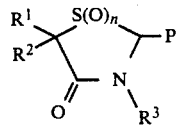

| Ex. No. | n | R¹— | R²— | R³— | P |
|---|---|---|---|---|---|
| 289 | 0 | " | " | " | CH₃ attached to pyridyl 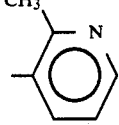 |
| 290 | 1 | " | " | " | " |
| 291 | 0 | " | " | " | Cl attached to pyridyl 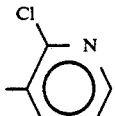 |
| 292 | 1 | " | " | " | " |
| 293 | 0 | " | " | " | pyridyl-Cl 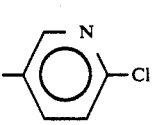 |
| 294 | 1 | " | " | " | " |

What is claimed is:

1. A method for treatment of a patient suffereing from a stress induced ulcer or an ulcer caused by gastric acid which comprises administering to said patient an antiulcerogenically effecitve amount of the compound represented by the following formula or a pharmaceutically acceptable salt thereof:

$$\begin{array}{c} R^1 \quad S(O)_n \\ R^2 \diagdown \diagup \diagdown P \\ | \quad | \\ O \diagup \diagdown N \diagdown R^3 \end{array}$$

wherein
R¹ is hydrogen or $C_1$–$C_6$ alkyl; R² is an unsubstituted or substituted member of the group consisting of aryl and aralkyl, in which the member, if substituted, is substituted by halogen, $C_1$–$C_6$ alkyl, $C_1$–$C_6$ alkoxy or halogenated $C_1$–$C_6$ alkyl; R³ is hydrogen, $C_1$–$C_6$ alkyl or $C_1$–$C_6$ alkyl substituted by halogen, amino, $C_1$–$C_6$ alkyl amino or di $C_1$–$C_6$ alkyl amino, $C_2$–$C_{20}$ alkenyl or $C_2$–$C_{20}$ alkylnyl;

P is an unsubstituted or substituted member of the group consisting of 3-pyridyl and 4-pyridyl in which the member, if substituted, is substituted by halogen or $C_1$–$C_6$ alkyl; and
n is 0 or 1.

2. A method according to claim 1 wherein R¹ is hydrogen; and P is 3-pyridyl.

3. A method according to claim 1 wherein R¹ is hydrogen, $C_1$–$C_6$ alkyl or $C_1$–$C_6$ alkyl substituted by halogen; and P is 3-pyridyl.

4. A method according to claim 1 wherein R¹ is hydrogen; R³ is hydrogen, $C_1$–$C_6$ alkyl or $C_1$–$C_6$ alkyl substituted by halogen; P is 3-pyridyl; and n is 0.

5. A method according to claim 1 wherein R¹ is hydrogen; R² is phenyl or phenyl substituted by halogen or $C_1$–$C_6$ alkoxy; R³ is hydrogen, $C_1$–$C_6$ alkyl or $C_1$–$C_6$ alkyl substituted by halogen; P is 3-pyridyl; and n is 0.

6. A method according to claim 1 which comprises administering to said patient an antiulcerogenically effective amount of the compound 5-(4-fluorophenyl)3-methyl-2-(3-pyridyl)thiazolidin-4-one or pharmaceutically acceptable salt thereof.

* * * * *